United States Patent
Srienc et al.

(10) Patent No.: US 7,901,937 B2
(45) Date of Patent: Mar. 8, 2011

(54) HIGH THROUGHPUT BIOREACTOR

(75) Inventors: Friedrich Srienc, Lake Elmo, MN (US); Abdelqader Zamamiri, Little Canada, MN (US); Nicholas R. Abu-Absi, Minneapolis, MN (US); James A. Kacmar, Lauderdale, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 104 days.

(21) Appl. No.: 12/264,044

(22) Filed: Nov. 3, 2008

(65) Prior Publication Data

US 2009/0081770 A1    Mar. 26, 2009

Related U.S. Application Data

(63) Continuation of application No. 10/286,941, filed on Nov. 1, 2002, now abandoned.

(60) Provisional application No. 60/337,398, filed on Nov. 2, 2001.

(51) Int. Cl.
*C12N 5/00* (2006.01)
*C12N 5/02* (2006.01)
*C12M 1/00* (2006.01)
*C12M 3/00* (2006.01)

(52) U.S. Cl. ............... 435/373; 435/288.7; 435/289.1; 435/305.1; 435/308.1; 435/325; 435/375; 435/383; 435/384

(58) Field of Classification Search ............... 435/288.7, 435/289.1, 305.1, 308.1, 373, 375, 325, 383, 435/384
See application file for complete search history.

(56) References Cited

U.S. PATENT DOCUMENTS

| | | | |
|---|---|---|---|
| 3,018,224 A | 1/1962 | Ferrari |
| 3,028,225 A | 4/1962 | Sheen |
| 3,674,672 A | 7/1972 | Whitesell |
| 3,714,445 A | 1/1973 | Blachere et al. |
| 4,024,393 A | 5/1977 | Braun et al. |
| 4,025,393 A | 5/1977 | Hirschfeld |
| 4,156,630 A | 5/1979 | Müller |
| 4,219,411 A | 8/1980 | Yen et al. |
| 4,242,447 A | 12/1980 | Findl et al. |

(Continued)

FOREIGN PATENT DOCUMENTS

EP     529666 A2 *   3/1993

(Continued)

OTHER PUBLICATIONS

Abu-Absi et al., "Application of a Flow Injection Flow Cytometry System for On-Line Monitoring of Bioreactors," Abstract, American Institute of Chemical Engineers, Reno, NV, Nov. 4-9, 2001. Available online May 28, 2001. [retrieved on Oct. 9, 2001]. Retrieved from the Internet: <URL:http://www.aiche.org/conferences/techprogram/paperdetail.asp?PaperID=2305&DSN=annual01>; 2 pgs.

(Continued)

*Primary Examiner* — Nathan A Bowers
(74) *Attorney, Agent, or Firm* — Mueting Raasch & Gebhardt, P.A.

(57) ABSTRACT

A continuous flow bioreactor system that includes a bioreactor, an optional post-bioreactor preparation chamber, a cell sorter, and an optional pre-bioreactor preparation chamber in a closed loop, useful for enriching a heterogeneous cell population growing in the bioreactor with an isolated subpopulation of cells.

12 Claims, 17 Drawing Sheets

U.S. PATENT DOCUMENTS

| | | | |
|---|---|---|---|
| 4,667,504 | A | 5/1987 | Hobson |
| 4,845,025 | A | 7/1989 | Lary et al. |
| 4,920,056 | A | 4/1990 | Dasgupta |
| 5,055,198 | A | 10/1991 | Shettigar |
| 5,330,914 | A | 7/1994 | Uhlen et al. |
| 5,411,708 | A | 5/1995 | Moscetta |
| 5,447,842 | A | 9/1995 | Simons |
| 5,888,807 | A | 3/1999 | Palsson et al. |
| 5,922,787 | A | 7/1999 | Kondo et al. |
| 6,103,956 | A | 8/2000 | Srienc et al. |
| 6,143,952 | A | 11/2000 | Srienc et al. |
| 6,156,570 | A * | 12/2000 | Hu et al. .............. 435/375 |
| 6,555,360 | B1 | 4/2003 | Srienc et al. |
| 6,770,470 | B2 | 8/2004 | Lee et al. |
| 6,890,487 | B1 | 5/2005 | Sklar et al. |
| 2002/0177227 | A1 | 11/2002 | Kraus et al. |
| 2003/0004299 | A1 | 1/2003 | Srienc et al. |
| 2003/0044832 | A1 | 3/2003 | Blankenstein |
| 2003/0096290 | A1 | 5/2003 | Fruehauf et al. |

FOREIGN PATENT DOCUMENTS

| | | |
|---|---|---|
| JP | 3160980 A | 7/1991 |
| NL | 7016218 | 5/1971 |
| WO | WO 00/24922 | 5/2000 |
| WO | WO 00/34433 | 6/2000 |
| WO | WO 01/14566 A2 | 3/2001 |

OTHER PUBLICATIONS

Abu-Absi et al., "Application of a Flow Injection Flow Cytometry System for On-Line Monitoring of Bioreactors," Presentation, American Institute of Chemical Engineers, Reno, NV, Nov. 4-9, 2001; 4 pgs.

Abu-Absi et al., "Application of a Flow Injection Flow Cytometry System for On-Line Monitoring of Bioreactors," Powerpoint Presentation, American Institute of Chemical Engineers meeting, Reno, NV, Nov. 4-9, 2001; 18 pgs.

Abu-Absi, Nicholas, "Analysis of Physiological State Parameters in Animal Cell Cultures," Doctoral Thesis, *University of Minnesota*, 2002; 176 pgs.

Abu-Absi et al., "Instantaneous evaluation of mammalian cell culture growth rates through analysis of the mitotic index," *J. Biotechnol.*, 2002;95(1):63-84.

Abu-Absi et al., "Automated Flow Cytometry for Acquisition of Time-Dependent Population Data," *Cytometry*, 2003;51A(2):87-96.

Alberghina et al., "Analysis of Microbiol Cells at the Single Cell Level—Why, How, When?" *J. Microbiol. Methods*. 2000;42(1):1-2.

Blanche et al., "Vitamin $B_{12}$: How the Problem of Its Biosynthesis Was Solved," *Angewandte Chemie Intl. Ed. Engl.*, 1995;34:383-411.

Blankenstein et al., "Coaxial Flow Mixer for Real-Time Monitoring of Cellular Responses in Flow Injection Cytometry," *Cytometry*, 1996;25:200-204.

Bratvold et al., "Analysis of the distribution of ingested bacteria in nanoflagellates and estimation of grazing rates with flow cytometry," *Aquatic Microbial Ecology*, 2000; 21:1-12.

Carlson et al., "Effects of Cofactor Imbalance on Pathway Fluxes in *Saccharomyces cerevisiae*," Abstract, American Institute of Chemical Engineers, Dallas, TX, Oct. 31-Nov. 5, 1999; [online] [retrieved on Sep. 3, 2002]. Retrieved from the Internet: <URL:http://www.aiche.org/ conferences/techprogram/paperdetail.asp?PaperID=2010 &DSN=annual9...>; 2 pgs.

Carlson et al., "Utilizing the Bi-directional GAL1-10 Promoter to Co-express Two Genes in *Saccharomyces cerevisiae*," Masters Thesis, *University of Minnesota*, St. Paul, MN, 1999; 107 pgs.

Carlson et al, "High level poly-beta-hydroxybutyrate production in *Saccharomyces cerevisiae*," Abstract of Poster Presentation, International Symposium on Biological Polyhydroxyalkanoates, Boston, MA, 2000; 1 pg.

Carlson et al., "Metabolic pathway analysis of *Saccharomyces cerevisiae* producing poly-beta-hydroxybutyric acid," Abstract of Oral Presentation, *Biotechnology*, 2000, International Biotechnology Symposium and Exhibition, Berlin, Germany, 2000; 1 pg.

Carlson et al., "Metabolic Pathway Analysis for Rational Strain Improvement," Abstract of Oral Presentation, American Institute of Chemical Engineers, Los Angeles, CA, Nov. 2000; [online], [retrieved on Mar. 7, 2003.]. Retrieved from the Internet: <URL:http://www.aiche.org/conferences/techprogram/paperdetail.asp?PaperID=2704&DSN=annual...>; 2 pgs.

Carlson, "Pathway analysis of *Saccharomyces cerevisiae* producing polyhydroxybutyrate (PHB) for strain improvement," [available online Mar. 23, 2001.] Biot 77 Abstract of Oral Presentation, ACS Conference, San Diego, CA, Apr. 1-5, 2001; 1 pg.

Carlson et al., "Pathway Analysis for Strain Improvement of *Saccharomyces cerevisiae* Producing Polyhydroxybutyrate (PHB)," Oral presentation with posters, ACS Conference, San Diego, Apr. 1-5, 2001; 30 pgs.

Carlson et al., "Anaerobic Production of Polyhydroxybutyrate (PHB) in *Saccharomyces cerevisiae*," Powerpoint Presentation, American Institute of Chemical Engineers meeting, Reno, NV, Nov. 4-9, 2001; 28 pgs.

Carlson et al., "Biochemical Network Modifications and Flux Analysis for Improved Poly-hydroxyalkanoate (PHA) Production in *S. cerevisiae*," Abstract and Powerpoint Presentation, Annual American Institute of Chemical Engineers meeting, Indianapolis, IN, Nov. 4-8, 2002. [online], [retrieved on Feb. 19, 2003]. Retrieved from the Internet: <URL:http://www.aiche.org/conferences/ techprogram/paperdetail.asp?PaperID=2715&DSN=annual02...>, 33 pgs.

Carlson et al., "Metabolic Pathway Analysis of a Recombinant Yeast for Rational Strain Development," *Biotechnol. Bioeng.*, 2002;79(2):121-134.

Cherlet et al., "Surface IgG Content of Murine Hybridomas: Direct Evidence for Variation of Antibody Secretion Rates During the Cell Cycle," *Biotechnol. Bioeng.*, 1995;47:535-540.

Cormack et al., "FACS-optimized mutants of the green fluorescent protein (GFP)," *Gene*, 1996;173:33-38.

Cubitt et al., "Understanding, improving and using green fluorescent proteins," *Trends Biochem. Sci.*, 1995;20:448-455.

deCrécy-Lagard et al., "Pristinamycin I Biosynthesis is *Streptomyces pristinaespiralis*: Molecular Characterization of the First Two Structural Peptide Synthetase Genes," *J. Bact.*, 1997;179(3):705-713.

Degelau et al., "Fluorometric measurement of poly-β hydroxybutyrate in *Alcaligenes eutrophus* by flow cytometry and spectrofluorometry," *Appl. Microbiol. Biotechnol.*, 1995;42:653-657.

Dien et al., "Bromodeoxyuridine Labeling and Flow Cytometric Identification of Replicating *Saccharomyces cerevisiae* Cells: Lengths of Cell Cycle Phases and Population Variability at Specific Cell Cycle Positions," *Biotechnol. Prog.*, 1991; 7(4):291-298.

Doi et al., "Nuclear Magnetic Resonance Studies on Poly(βhydroxybutyrate) and a Copolyester of β-Hydroxybutyrate and β-Hydroxyvalerate Isolated from *Alcaligenes eutrophus* H16," *Macromolecules*, 1986;19:2860-2864.

Döring et al., "Reassigning Cysteine in the Genetic Code of *Escherichia coli*," *Genetics*, 1998;150:543-551.

Döring et al., "Enlarging the Amino Acid Set of *Escherichia coli* by Infiltration of the Valine Coding Pathway," *Science*, 2001;292:501-504.

Dunlop et al., "Micromixing in Fermentors: Metabolic Changes in *Saccharomyces cerevisiae* and Their Relationship to Fluid Turbulence," *Biotechnol. Bioeng.*, 1990;36:854-864.

Edwards et al., "Plug Flow Cytometry: An Automated Coupling Device for Rapid Sequential Flow Cytometric Sample Analysis," *Cytometry*, 1999;37:156-159.

Edwards et al., "Plug Flow Cytometry Extends Analytical Capabilities in Cell Adhesion and Receptor Pharmacology," *Cytometry*, 2001;43:211-216.

Fowler et al., "Effects of Reactant Heterogeneity and Mixing on Catabolite Repression in Cultures of *Saccharomyces cerevisiae*," *Biotechnol. Bioeng.*, 1989;33:1039-1046.

Fredrickson et al., "Statistics and Dynamics of Procaryotic Cell Populations," *Math. Biosci.*, 1967;1:327-374.

Fredrickson, et al., "A Statistical Analysis of Flow Cytometric Determinations of Phagocytosis Rates," *Cytometry*, 1992;13(4):423-431.

Frykman et al., "Quantitating Secretion Rates of Individual Cells: Design of Secretion Assays," *Biotechnol. Bioeng.*, 1998;59(2):214-226.

Frykman et al., "Cell Cycle-Dependent Protein Secretion by *Saccharomyces cerevisiae*," *Biotechnol Bioeng.*, 2001;76(3):259-268.

Galbraith et al., "Flow Cytometric Analysis and FACS Sorting of Cells Based on GFP Accumulation," *Methods in Cell Biology*, 1999;58:315-341.

Gao et al., "Characterization of Heterologous and Native Enzyme Activity Profiles in Metabolically Engineered *Zymomonas mobilis* Strains During Batch Feinientation of Glucose and Xylose Mixtures," *Appl. Biochem. Biotechnol.*, 2002;98-100:341-355.

Gocze et al., "Factors Underlying the Variability of Lipid Droplet Fluorescence in MA-10 Leydig Tumor Cells," *Cytometry*, 1994;17:151-158.

Gorenflo et al., "Quantification of bacterial polyhydroxyalkanoic acids by Nile red staining," *Appl. Microbiol. Biotechnol.*, 1999;51:765-772.

Hahn et al., "Growth Kinetics, Nutrient Uptake, and Expression of the *Alcaligenes eutrophus* Poly(β-hydroxybutyrate) Synthesis Pathway in Transgenic Maize Cell Suspension Cultures," *Biotechnol. Prog.*, 1997;13:347-354.

Hall, "Adaptive mutations in *Escherichia coli* as a model for the multiple mutational origins of tumors," *Proc. Natl. Acad. Sci. USA*, 1995;92:5669-5673.

Hatzis et al., "Cell-Cycle Analysis in Phagotrophic Microorganisms from Flow Cytometric Histograms," *J. Theor. Biol.*, 1997;186:131-144.

Herzenberg et al., "Monoclonal antibodies and the FACS: complementary tools for immunobiology and medicine," *Immunology Today*, 2000;21(8):383-390.

Kacmar et al., "Monitoring PHB Synthesis in *Saccharomyces cerevisiae* using Flow Cytometry," Abstract of Oral Presentation, American Institute of Chemical Engineers, Indianapolis, IN, Nov. 4-8, 2002; [online], [retrieved on Feb. 19, 2003]. Retrieved from the Internet: <URL:http://www.aiche.org/conferences/techprogram/paperdetail.asp?PaperID=1919&DSN=annual02>; 2 pgs.

Kacmar et al., "Staining of Polyhydroxybutyrate for Cytometric Analysis," Powerpoint Presentation, American Institute of Chemical Engineers meeting, Indianapolis, IN, Nov. 4-8, 2002; 27 pgs.

Kacmar et al., "Single-cell variability in growing *Saccharomyces cerevisiae* cell populations measured with automated flow cytometry," *J. Biotechnol.*, Apr. 28, 2004;109(3):239-254.

Kacmar et al., "Dynamics of single cell property distributions in Chinese hamster ovary cell cultures monitored and controlled with automated flow cytometry," *J. Biotechnol.*, Dec. 6, 2005;120(4):410-420. Available online Sep. 6, 2005.

Kacmar et al., "Staining and quantification of poly-3-hydroxybutyrate in *Saccharomyces cerevisiae* and Cupriavidus necator cell populations using automated flow cytometry," *Cytometry A*, Jan. 2006;69(1):27-35.

Kacmar et al., "The cytostat: A new way to study cell physiology in a precisely defined environment," *J. Biotechnol*, Nov. 1, 2006;126(2):163-172. Available online May 22, 2006.

Kelley, "Sample Station Modification Providing On-line Reagent Addition and Reduced Sample Transit Time for Flow Cytometers," *Cytometry*, 1989;10:796-800.

Kelley et al., "Controlled Synthesis of Polyhydroxyyalkanoic (PHA) Nanostructures in *R. eutropha*," NANO Lett., 2001;1(9):481-485.

Kromenaker at al., "Cell-Cycle-Dependent Protein Accumulation by Producer and Nonproducer Murine Hybridoma Cells Lines: A Population Analysis," *Biotechnol. Bioeng.*, 1991;38:665-677.

Kromenaker et al., "Stability of Producer Hybridoma Cell Lines after Cell Sorting: A Case Study," *Biotechnol. Prog.*, May-Jun. 1994;10(3):299-307.

Kromenaker et al., "Effect of lactic acid on the kinetics of growth and antibody production in a murine hybridoma: secretion patterns during the cell cycle," *J. Biotechnol.*, Apr. 30, 1994;34(1):13-34.

Kromenaker et al., "Cell cycle kinetics of the accumulation of heavy and light chain immunoglobulin proteins in a mouse hybridoma cell line," *Cytotechnology*, 1994;14(3):205-218.

Kuckuck et al., "High Throughput Flow Cytometry," *Cytometry*, 2001;44:83-90.

Lavin et al., "Flow Cytometric Measurement of Rates of Particle Uptake from Dilute Suspensions by a Ciliated Protozoan," *Cytometry*, 1990;11(8):875-882.

Leaf et al., "*Saccharomyces cerevisiae* expressing bacterial polyhydroxybutyrate synthase produces poly-3-hydroxybutyrate," *Microbiol. UK*, 1996;142:1169-1180.

Leaf, "Engineering Yeast for Polyhydroxybutyrate Production," Doctoral Thesis, *University of Minnesota*, 1998; 171 pgs.

Leaf et al., "Metabolic Modeling of Polyhydroxybutyrate Biosynthesis," *Biotechnol. Bioeng.*, 1998;57(5):557-570.

Leelavatcharamas et al., "Monitoring the Proliferative Capacity of Cultured Animal Cells by Cell Cycle Analysis," *Flow Cytometry Applications in Cell Culture*, New York, NY, 1996; 1-15.

Lindberg et al., "Flow Injection Cytometry: A New Approach for Sample and Solution Handling in Flow Cytometry," *Cytometry*, 1993;14:230-236.

Mantzaris et al., "Numerical solution of multi-variable cell population balance models. I. Finite difference methods," *Comp. & Chem. Eng.*, 2001;25:1411-1440.

Mantzaris et al., "Numerical solution of multi-variable cell population balance models. II. Spectral methods," *Comp. & Chem. Eng.*, 2001;25:1441-1462.

Mantzaris et al., "Numerical solution of multi-variable cell population balance models. III. Finite element methods," *Comp. & Chem. Eng.*, 2001;25:1463-1481.

Mantzaris et al., "Optimal Carbon Source Switching Strategy for the Production of PHA Copolymers," *AIChE J.*, 2001;47(3):727-743.

Mantzaris et al., "Nonlinear productivity control using a multi-staged cell population balance model," *Chemical Engineering Science*, 2002;57:1-14.

Mazel et al., "Genetic characterization of polypeptide deformylase, a distinctive enzyme of eubacterial translation," *EMBO J.*, 1994;13:914-923.

Mittendorf et al., "Synthesis of medium-chain-length polyhydroxyalkanoates in *Arabidopsis thaliana* using intermediates of peroxisomal fatty acid β-oxidation," *Proc. Natl. Acad. Sci. USA*, 1998;95:13397-13402.

Müller et al., "A flow cytometric approach for characterization and differentiation of bacteria during microbial processes," *Appl. Microbiol. Biotechnol.*, 1995;43:93-101.

Müller et al., "Adaptive responses of *Ralstonia eutropha* to feast and famine conditions analysed by flow cytometry," *J. Biotechnol.*, 1999;75:81-97.

Münch et al., "The decisive role of the *Saccharomyces cerevisiae* cell cycle behaviour for dynamic growth characterization," *J. Biotechnol.*, 1992;22:329-352.

Natarajan, "Determination of physiological state parameters of growing cell populations," Ph.D. Thesis, *University of Minnesota*, St. Paul, MN, 1999; 304 pgs.

Natarajan et al., "Comparison of mutant forms of the green fluorescent protein as expression marks in Chinese hamster ovary (CHO) and *Saccharomyces cerevisiae* cells," *J. Biotechnol.*, 1998;62:29-45.

Natarajan et al., "Flow cytometric analysis of growth of two *Streptoccocus gordonii* derivatives," *J. Microbiol. Meth.*, 1999;34:223-233.

Natarajan et al., "Dynamics of Glucose Uptake by Single *Eschirichia coli* Cells," *Metabolic Engineering*, 1999;1:320-333.

Natarajan et al., "Glucose uptake rates of single *E. coli* cells grown in glucose-limited chemostat cultures," *J. Microbiol. Methods*, 2000;42(1):87-96.

Omann et al., "A Convenient On-line Device for Reagent Addition, Sample Mixing, and Temperature Control of Cell Suspensions in Flow Cytometry," *Cytometry*, 1985;6:69-73.

Patkar et al., "Flow cytometry as a useful tool for process development: rapid evaluation of expression systems," *J. Biotechnol.*, 2002;93(3):217-229.

Pennings et al., "Improved Flow Cytometry of Cellular DNA and RNA by On-Line Reagent Addition," *Cytometry*, 1987;8:335-338.

Ramkrishna et al., "On Relationships Between Various Distribution Functions in Balanced Unicellular Growth," *Bull. Math. Biophys.*, 1968;30:319-323.

Ramkrishna, "Statistical Models of Cell Populations," *Advances in Biochemical Engineering*, Ghose et al., Eds., Springer-Verlag, New York, 1979; pp. 1-47.

Ramkrishna, "The Status of Population Balances," *Rev. Chem. Eng.*, 1985;2:49-95.

Ramkrishna et al., "In Honor of Arnold G. Fredrickson," *J. Biotechnol.*, 1999; 71:3-5.

Reed, "Flow Injection Analysis in Bioprocess Control," in *Sensors in Bioprocess Control*, Twork et al., Eds., New York, 1990:221-241.

Richaud et al., "Directed Evolution of Biosynthetic Pathways: Recruitment of Cysteine Thioethers for Constructing the Cell Wall of *Escherichia coli*," *J. Biol. Chem.*, Dec. 25, 1993;268(36):26827-26835.

Riis et al., "Gas chromatographic determination of poly-β-hydroxybutyric acid in microbial biomass after hydrochloric acid propanolysis," *Journal of Chromatography*, 1988;445:285-289.

Ruzicka et al., "Flow Injection Analyses. Part I. A New Concept of Fast Continuous Flow Analysis," *Anal. Chim. Acta.*, Aug. 1975;78(1):145-157.

Ruzicka et al., "Flow Injection Cytoanalysis," *Anal. Chem.*, May 1, 1992;64(9):537-544.

Sambrook et al., *Molecular Cloning: A Laboratory Manual*, Books 1-3, Cold Spring Harbor Laboratory Press, Cold Spring Harbor, NY, 1989; title page, publisher's page and table of contents only:28 pgs.

Scheper et al., "On-line and Off-line Process Analysis," in *Mammalian Cell Biotechnology in Protein Production*, Hauser et al., Eds., Walter de Gruyter, Berlin, New York, 1997:373-410.

Schmidt, *The Engineering of Chemical Reactions*, New York, NY, 1998; cover page, title page and table of contents only, 9 pgs.

Schmidt-Dannert, Claudia, "Acquisition of Instrumentation for Automated Cell Screening and Characterization" Grant\ Abstract, Grant No. DBI-0079864 [online]. National Science Foundation, Biological Infrastructure, Aug. 1, 2000 to Jul. 31, 2002, [retrieved on Mar. 11, 2004]. Retrieved from the Internet: <URL: https://www.fastlane.nsf.gov/servlet/showaward?award=0079864>; 2 pgs.

Sen et al., "Flow cytometric study of hybridoma cell culture: correlation between cell surface fluorescence and IgG production rate," *Enzyme Microb. Technol.*, Aug. 1990;12(8):571-576.

Sitton et al., "Transient gene expression in CHO cells monitored with automated flow cytometry," *Cytotechnol.*, Sep. 2006;52(1):13-24. Available online Nov. 22, 2006.

Srienc et al., "Characterization of Intracellular Accumulation of Poly-β-Hydroxybutyrate (PHB) in Individual Cells of *Alcaligenes eutrophus* H16 by Flow Cytometry," *Biotechnol. Bioeng.*, Aug. 1984;26(8):982-987.

Srienc et al., "Flow Cytometry Analysis of Recombinant *Saccharomyces cerevisiae* Populations," *Cytometry*, 1986;7(2):132-141.

Srienc et al., "Kinetics of the Cell Cycle of *Saccharomyces cerevisiae*," *Ann. NY Acad. Sci.*, Oct. 13, 1992;665:59-71.

Srienc, "Cytometric data as the basis for rigorous models of cell population dynamics," *Journal of Biotechnology*, 1999; 71:233-238.

Srienc, Friedrich, "Development of On-line Flow Cytometry" Grant Abstract, Grant No. BES-9986029 [online]. National Science Foundation, Bioengineering and Environmental Systems, Oct. 1, 2000 to Sep. 30, 2002, [retrieved on Mar. 7, 2003]. Retrieved from the Internet: <URL: https://www.fastlane.nsf.gov/servlet/showaward?award=9986029>; 1 pg.

Srienc et al., "Metabolic Engineering of Polyhydroxyalkanoate Synthesis in Eukaryotic Cells," Proceed. of the 2000 Agric. Biotechnol. Symp., 2000;13 pgs.

Srienc, Friedrich, "Novel Processes for Biopolymer Production," Grant Abstract, Grant No. BES-0109383 [online]. National Science Foundation, Bioengineering and Environmental Systems, Nov. 1, 2001 to Oct. 31, 2004 [retrieved on Aug. 23, 2002]. Retrieved from the Internet:<URL:https://www.fastlane.nsf.gov/servlet.showaward? award=0109383>; 2 pgs.

Steff et al., "Detection of a Decrease in Green Fluorescent Protein Fluorescence for the Monitoring of Cell Death: An Assay Amenable to High-Throughput Screening Technologies," *Cytometry*, 2001;45:237-243.

Subramanian et al., "Quantitative analysis of transient gene expression in mammalian cells using the green fluorescent protein," *J. Biotechnol.*, 1996;49: 137-151.

Subramanian et al., "The Green Fluorescent Protein (Gfp) as a Tool for the Analysis of Gene Expression in Mammalian Cells," in *Cell & Tissue Culture: Laboratory Procedures*, Doyle et al., Eds., Chichester, England, 1997; pp. 9B:1.1 to 9B1.14.

Sudesh et al., "Synthesis, structure and properties of polyhydroxyalkanoates: biological polyesters," *Progress in Polymer Science*, Dec. 2000; 25(10):1503-1555.

Taylor, "Dispersion of soluble matter in solvent flowing slowly through a tube," *Proceedings of the Royal Society of London (Series A), Mathematical and Physical Sciences*, Aug. 25, 1953;219(1137):186-203.

Thibaut et al., "Biosynthesis of vitamin $B_{12}$: Isolation of precorrin-6x, a metal-free precursor of the corrin macrocycle retaining five 5-adenosylmethionine-derived peripheral methyl groups," *Proc. Natl. Acad. Sci. USA*, Nov. 1990; 87(22):8795-8799.

Zamamiri, Abdelqader, "Analysis of Oscillating Yeast Cultures," Masters Thesis, *Louisiana State University and Agricultural & Mechanical College*, 1998; 73 pgs.

Zamamiri, Abdelqader, "Analysis and Mathematical Modeling of Autonomously Oscillating Yeast Cultures," Doctoral Dissertation, *Louisiana State University and Agricultural & Mechanical College*, 2001; 157 pgs.

Zamamiri et al., "High Throughput Screening in a CSTR: Application of an Old Theory for a New Problem," American Institute of Chemical Engineers, Reno, NV, Nov. 4-9, 2001. Available online May 24, 2001. [retrieved on Oct. 9, 2001]. Retrieved from the Internet: <URL: http://www.aiche.org/ conferences/techprogram/paperdetail.asp?PaperID=3083&DSN=annual01>; 2 pgs.

Zamamiri et al., "High Throughput Screening in a CSTR: Application of an Old Theory to a New Problem," Powerpoint presentation, American Institute of Chemical Engineers meeting, Reno, NV, Nov. 4-9, 2001; 24 pgs.

Zamamiri et al., "Automated Online Flow Cytometry," International Society for Analytical Cytology XXI International Congress, San Diego, CA, May 4-9, 2002; 21 pgs.

Zamamiri et al., "Development of On-line Flow Cytometry," American Institute of Chemical Engineers, Indianapolis, IN, Nov. 4-8, 2002 [online], [retrieved on Feb. 19, 2003]. Retrieved from the Internet:<URL:http://www.aiche.org/ conferences/ techprogram/paperdetail.asp?PaperID=1392&DSN=annual02>; 2 pgs.

Zhao, "The Design of a Flow Injection Flow Cytometry System for On-line Assessment of Single-cell Level Property Distributions in Cell Populations," Masters Thesis, *University of Minnesota*, St. Paul, MN, 1997; 185 pgs.

Zubay, *Biochemistry*, $3^{rd}$ Ed., Wm. C. Brown, Dubuque, Iowa, 1993; cover page, title page and table of contents only, 17 pgs.

* cited by examiner

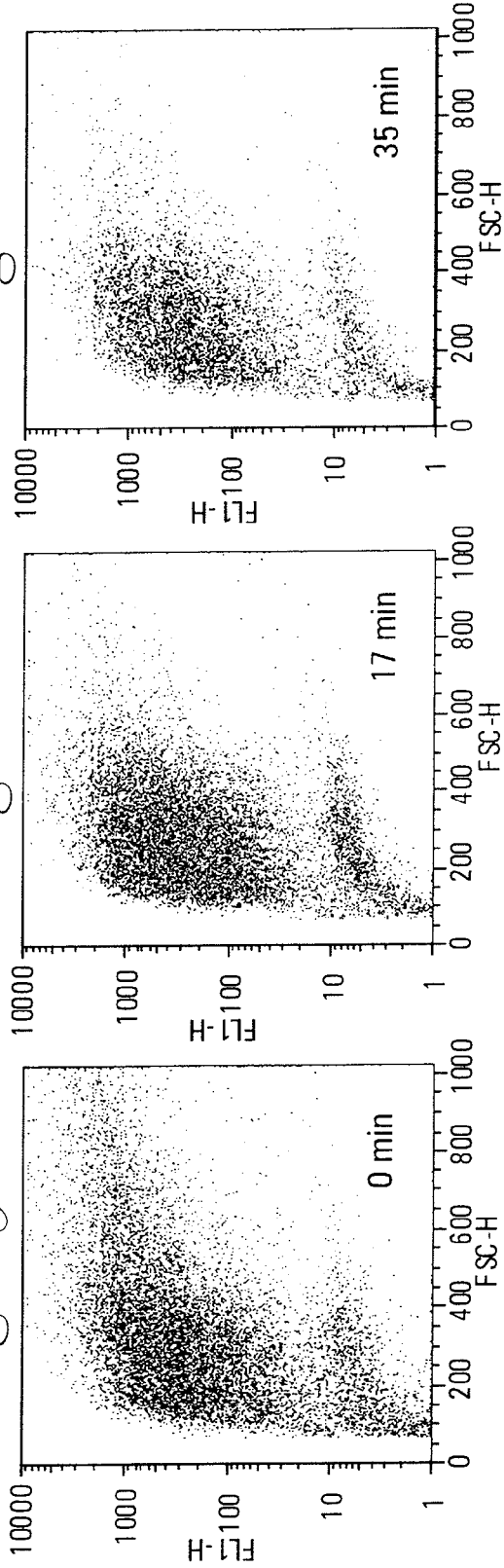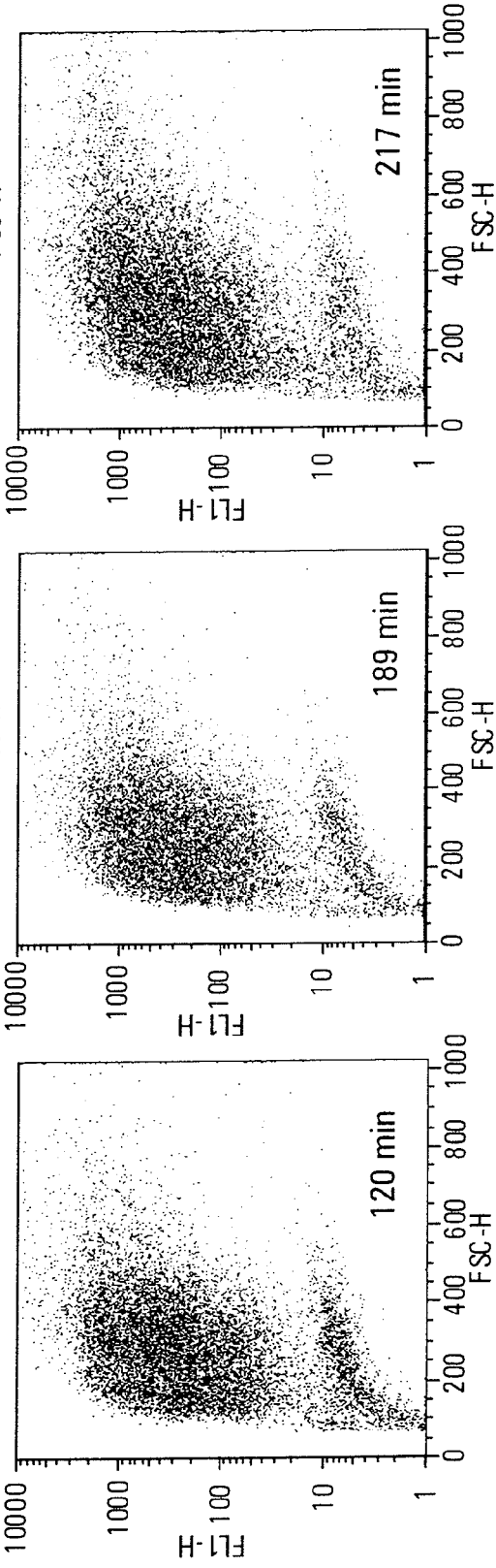

HIGH THROUGHPUT BIOREACTOR

This application is a continuation application of Ser. No. 10/286,941, filed on Nov. 1, 2002, which claims the benefit of U.S. Provisional Application Ser. No. 60/337,398, filed Nov. 2, 2001, each of which is incorporated herein by reference in its entirety.

GOVERNMENT FUNDING

This invention was made with government support under a grant from the National Science Foundation, Grant No. BES-9986029 and DBI-0079827. The U.S. Government has certain rights in this invention.

TECHNICAL FIELD

The invention relates to bioreactors and, more particularly, techniques for high throughput in bioreactor design and operation.

BACKGROUND

Recent molecular biology techniques permit a systematic introduction of mutations into specific genes. The success of such molecular evolution techniques depends greatly on the ability to recognize and isolate engineered cells that contain specific mutations. A considerable effort has been made to develop robots that can automatically carry out manipulations for the purpose of isolating specific rare cells, e.g., mutant cells that possess a desired phenotype. There are currently several so-called high throughput-screening systems commercially available. These systems attempt to automate repetitive manual laboratory operations for isolating specific rare cells of interest.

Isolation of these rare cells is not always possible. Often separation inaccuracies occur which result in contamination of the isolated rare cells of interest with other nonmutated or nonengineered cells. When the rare cells are cultured, the contaminating cells typically dominate the culture and proliferate more successfully than the rare cell type. The isolation procedure often results in a culture that is no more rich in rare cells than at the start of the isolation procedure.

SUMMARY

The present invention allows for the progressive enrichment of the cell culture in a bioreactor for rare cells of interest. The present invention also reduces the competitive pressure of other cells that may be present in the bioreactor. The invention includes a bioreactor system that has one or more bioreactors, optional post-bioreactor and pre-bioreactor preparation chambers to process cells, and cell sorters, preferably flow cytometers, that receive and separate the processed cells to either a waste stream or back to the bioreactor(s). The entire system operates in a continuous mode, so that inaccuracies in separation are not as detrimental to the overall performance of the system in isolating and growing the rare cells of interest as they are in a successive batch mode system. If more than one bioreactor is used, the system can be multiplexed.

The present invention therefore provides a system for enriching the cell culture in a bioreactor with an isolated subpopulation of cells. The bioreactor is capable of providing an environment for growing a heterogeneous population of cells. Any desired cell type can be used in the bioreactor. The cells can be prokaryotic or eukaryotic and include, without limitation, bacteria, protozoa, fungal cells, invertebrate cells such as insect cells, and vertebrate cells such as mammalian cells, including human cells. Cell types of industrial or clinical significance can be used with the present invention, such as hybridoma cells, omnipotent or pluripotent stem cells, differentiated stem cells, hamster CHO cells. The bioreactors are supplied with a growth medium and/or additives that promote the growth and proliferation of the cells. It will be understood that the rate of enrichment will depend, for example, on cell type, cell division rate and the time needed to pretreat the cells in the pre-bioreactor preparation chamber, if any, prior to monitoring and sorting.

In one embodiment, a continuous stream of the heterogeneous population of cells is removed from the bioreactor and delivered to an optional post-bioreactor preparation chamber coupled to the bioreactor. The post-bioreactor preparation chamber prepares the heterogeneous population of cells in the continuous stream for separation. Cells in the continuous stream can be prepared for separation by, for example, diluting, concentrating, and/or selectively staining cells that possess specific markers or identifiers. Optionally, multiple post-bioreactor preparation chambers can be used in series or in parallel. For example, multiple bioreactor preparation chambers can be used in series to perform different functions on the cells prior to sorting. Post-bioreactor preparation chambers can be used, for example, to increase flow through the cell sorter.

The prepared heterogeneous population of cells in the continuous stream is then separated into subpopulations of cells based on cell characteristics. In one embodiment, a flow cytometer coupled to the post-bioreactor preparation chamber is used to separate the cells into separate subpopulations of cells. Other examples of sorting procedures that can be carried out using a cell sorter include settling, total cell recycling, and magnetic separation, however, none of these techniques are capable of isolating specific subpopulations of cells as quickly and efficiently as a flow cytometer. Optionally, multiple flow cytometers are used in series or in parallel to sort cells, for example cells having multiple or alternative identifiable phenotypes.

Once separated in the flow cytometer, a subpopulation of cells in the continuous stream is provided to an optional pre-bioreactor preparation chamber. The pre-bioreactor preparation chamber prepares the separated subpopulation of cells, for example by concentrating them, and returns the subpopulation of cells to the bioreactor. Multiple pre-bioreactor preparation chambers can be used, in series or in parallel, as needed.

Additives can be provided or withheld to selectively promote the growth of one or more cell types over other cell types in the one or more bioreactors further enhancing the enrichment process.

BRIEF DESCRIPTION OF FIGURES

FIGS. 14A-14F are cytograms plotting forward scatter (FSC) against green fluorescent protein (GFP) fluorescence for yeast cells of FIG. 11 grown in a bioreactor system.

DETAILED DESCRIPTION OF ILLUSTRATIVE EMBODIMENTS

Figure 1:
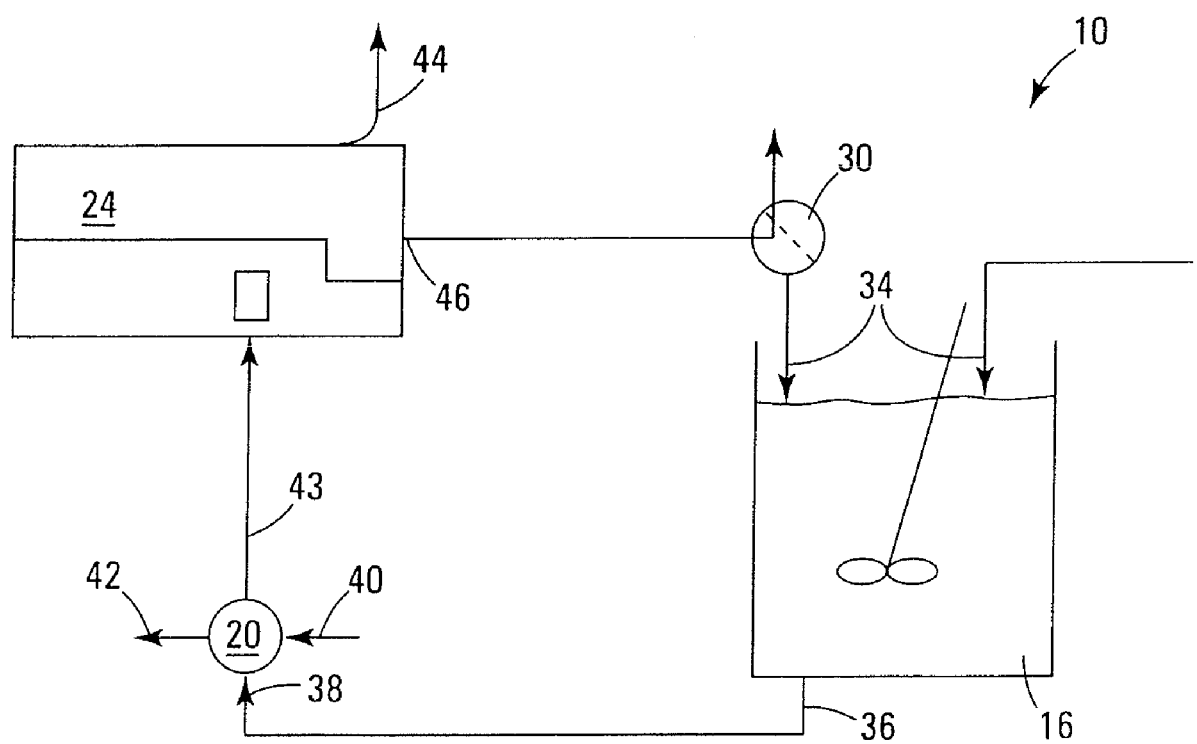
FIG. 1 is an example of a bioreactor system according to the present invention.

In the following detailed description of the embodiments, reference is made to drawings that form a part hereof, and in which are shown by way of illustration specific embodiments in which the invention may be practiced. It is to be understood that other embodiments may be utilized and processing step/structural changes may be made without departing from the scope of the present invention.

In bioreactors, heterogeneity is one of the predominant characteristics of cell cultures. Individual cells within the cell population have different sizes, chemical structures, DNA contents, production and secretion rates of proteins, etc. In order to enhance the overall productivity of a bioreactor, it is frequently desirable to isolate and enrich the bioreactor with a subpopulation of cells that possess one or more specific advantageous properties.

The present invention provides a bioreactor system and method of operation that can be used to enrich a heterogeneous cell population with cells having an identified distinguishable phenotype. High throughput screening allows the heterogeneous cell population to be continuously analyzed and sorted for the identified phenotype and recycled in a bioreactor to rapidly enrich the cell culture for the cells of interest. The system can also be used to alter and control the steady state cell fractions in mixed cultures through cell sorting and recycling as an alternative to applying the common external selective pressures.

Cells are sorted based upon a detectable difference in phenotype between the rare cell of interest (i.e., the mutant or engineered cell) and the rest of the cell culture population (i.e., the "wild-type" or non-mutant cells). Cell sorting is preferably accomplished using a flow cytometer. An optical flow cytometer is used to sort cells based upon differences in light absorption, light scattering, or excitation such as fluorescence or phosphorescence. For example, cells can be sorted based on differences in UV absorption or fluorescence. An acoustic flow cytometer is used to sort cells based upon differences in acoustic properties of the cells. It is intended that other cell sorting techniques based on other differentiable properties of the cells such as magnetic, electromagnetic, radiation, enzymatic or chemical properties of the cell can also be used. Thus, cell sorters capable of carrying out these other sorting functions can be used instead of, or in addition to, a flow cytometer.

In some applications cells need to be stained prior to sorting in order to make the differences in phenotype optically detectable. Any cellular component can be stained. The staining can be internal to or external to the cell. If the cellular component is intracellular, the staining agent is able to cross the cell membrane, for example by diffusion, endocytosis, or facilitated transport. Preferably, staining agents that do not adversely affect the viability or metabolism of the living cells are used. For example, cells can be stained using antibodies, preferably antibodies that bind to the surface of the cell. Intracellular stains include stains for DNA, and nile red (which stains organic molecules such as polyhydroxybutyrate). The staining reagent can be a protein or other ligand that attaches to a membrane receptor and then is optionally taken into the intracellular compartment. As another example, cells having altered metabolism of glucose can be stained by feeding the cells in the post-bioreactor preparation chamber a selected glucose analog that contains an optically detectable moiety that accumulates inside the cell.

In other applications, the cells do not require staining or other post-bioreactor preparation. In these applications, the cells may inherently possess one or more features that, without additional treatment, can be used in distinguishing and separating the cells of interest. Thus, for example, differences in phenotype can be detected without the need for staining the cells. For example, cells can be recombinantly engineered to express a marker protein, such as green, blue or red fluorescent protein (GFP, BFP or RFP), which is optically detectable without the need additional staining. Even if the post-bioreactor preparation chamber is not needed to stain or otherwise mark the cells prior to sorting, it may be useful for adjusting and/or optimizing the concentration of the cells, if needed, prior to sorting.

The technology described herein may be used for commercial fermentations or in various types of research, such as pharmaceutical, medical and biotechnology research. Medical applications include stem cell research (e.g., separating a single type of stem cells from a mixture of such cells for further study or cultivation), cancer research, infectious disease research, preparation of cells to be used in transplantation (e.g., isolation of desired cells with purging of undesired cells), and drug discovery. As an example of an industrial application, DNA shuffling can be used to enhance, alter or achieve an enzymatic activity that results in a detectable phenotype, such as increased production of polyhydroxyalkanoate (PHA). This metabolite can be stained in the post-bioreactor preparation chamber using nile red, and cells containing this metabolite can thus be detected.

Biochemical engineering principles and tools have been used in addressing the screening and bioseparation problems described herein. The isolation of specific mutant cells can be efficiently achieved using a continuous stirred tank reactor with cell recycling. A continuous flow within the system is maintained to allow for recycling of a subpopulation of selected cells. The equipment is coupled in such a way as to allow for extended monitoring of the cell culture growing in the bioreactor system. The equipment preferably forms a closed system such that the cells are not exposed to unsterile surroundings at any time. In a closed system, cells will not contaminate the unsterile surroundings and likewise the continuous culture will not be contaminated by agents in the surrounding environment. Thus, the closed system can be used to maintain a sterile environment in which to grow and enrich the selected subpopulation of cells.

The theory of competition in mixed cell cultures can be used to predict the cell growth dynamics in the bioreactor system of the present invention. Based on this approach the operating conditions of the bioreactor can be optimized to isolate specific mutants in the shortest possible time. Model simulations indicate that the time required for enriching the bioreactor with mutant cells is determined largely, if not solely, by the initial system dynamics. The major factors affecting these dynamics are the initial fraction of mutant cells in the bioreactor, the ratio of their specific growth rate to that of the "wild type" (i.e., nonmutant or nonengineered) cells and the operating conditions. The analysis and sorting rate of the flow cytometer, on the other hand, play only a minor role in determining the system early response. However, as the fraction of mutant cells increase the analysis and sorting capabilities of the flow cytometer become limiting. By following the optimal operation path, the fraction of mutant cells in a bioreactor can be increased from 10 to 0.9 in less than about two days. These findings hold even if the mutant cells grow at a rate 30% less than that of the wild type cells.

Enrichment by way of cell sorting followed by recycling is somewhat counterintuitive. The sorting process is not perfect and cannot, of itself, eliminate all unwanted (i.e., wild-type) cells. Therefore, cells of interest (e.g., mutant cells) are returned to the culture along with some wild-type cells. If these sorted cells were instead delivered to a batch culture, it is more likely that the batch culture would eventually become overgrown with wild-type cells, particularly if their growth rate is faster. It would then be necessary to subject the batch culture again to the flow cytometry analysis and the sorting process. In contrast, because the continuous culture continuously examines the presence of the desired cells in the outflow of the reactor and sorts them back into the reactor, undesired cells (e.g. wild-type cells) are diluted out by the continuous operation of the reactor. Significant enrichment is therefore expected using the continuous flow recycling system described herein.

The present invention has several advantages over previous cell sorting systems. One advantage is speed: the calculations outlined above suggest that enrichment occurs much more quickly than would have been otherwise expected. In addition, the use of a closed system makes contamination much less likely than in open systems, as the cells in the closed system are not exposed to unsterile surrounding at any time, so the cells do not contaminate the unsterile surroundings and the continuous culture likewise will not be contaminated.

FIG. 1 shows one example of a bioreactor system 10 according to the present invention. The present example includes at least one bioreactor 16, post-bioreactor preparation chambers 20, a flow cytometer 24 and pre-bioreactor preparation chambers 30. In the present example, the components of the bioreactor system 10 are coupled together to provide a closed system that can maintain a sterile environment within the system 10.

The bioreactor 16 is capable of providing an environment for growing a heterogeneous population of cells. For example, the bioreactor 16 can include the ability to stir the growth medium and cells contained in the bioreactor 16. Stirring the bioreactor 16 contents can be, for example, through the use of a magnetic stir bar, or through the use of a stir shaft built into the structure of the bioreactor 16. In addition, the bioreactor 16 can further include one or more ports through which the bioreactor can be inoculated with cells and/or measurements of the medium can be made (e.g., temperature, pH, dissolved $CO_2$, dissolved $O_2$ of the bioreactor content). Bioreactor 16 further includes inlet ports 34 through which recycled cells in medium and fresh medium and/or other liquids can be introduced into the bioreactor 16, and an outlet port 36 through which cells in medium can be withdrawn from the bioreactor 16.

In operating the present bioreactor system 10, the bioreactor 16 is filled with the appropriate growth medium. The medium is sterilized through any of a number of known techniques. These techniques can include, but are not limited to, sterilization through filtration of the medium into a sterilized bioreactor 16 or autoclaving of the bioreactor 16 containing the growth medium. After sterilization, the bioreactor 16 is inoculated with the cell population of interest. The population of the inoculated cells can be allowed to increase to a threshold density level, which becomes the cell density at which the bioreactor system 10 is maintained (i.e., the steady state of the cell density in the system 10).

To maintain this steady state cell density in the system 10, a continuous stream of the heterogeneous population of cells and the medium is removed from the bioreactor 16 through the outlet port 36, and recycled cells and medium are introduced into the bioreactor 16 through the inlet ports 34. The continuous stream of cells and medium are transported to the post-bioreactor preparation chambers 20. The post-bioreactor preparation chambers 20 include two inlet ports 38 and 40, and two outlet ports 42 and 43. The post-bioreactor preparation chambers 20 prepare the cells in the continuous stream of cells for separation in the flow cytometer 24. The design of the preparation chambers allows for in-line preparation of the cells discharged from the bioreactor 16 prior to their analysis and separation in the flow cytometer 24. The effluent stream from the bioreactor is loaded into the preparation chambers 20 through inlet port 38, where the cells can undergo a number of preparatory steps before injection to the flow cytometer 24.

These preparation steps can include, but are not limited to, adjusting the cell concentration, cell washing, and cell staining. Appropriate reagents for performing these preparation steps can be introduced into the preparation chambers 20 through inlet port 40. Non-cell waste products from these steps are removed from chambers 20 through outlet port 42. Outlet port 43 connects chambers 20 to the flow cytometer 24.

An example of a preparation chamber is discussed in a U.S. pat. application entitled "A Flow Injection Flow Cytometry System for On-line Monitoring of Bioreactors and Method for Monitoring", application Ser. No. 09/280,757 filed on Mar. 29, 1999, which is based on U.S. Provisional Pat. App. Ser. No. 60/079,970 filed on Mar. 30, 1998. The preparation chamber is designed for cell sample processing. The design of the preparation chamber allows not only an accurate on-line dilution but also on-line cell staining, and washing. In one aspect, the chamber represents a stirred tank reactor with ports that serve as inlets and outlets. Since dilution, staining processes, and other enzymatic reactions are basically mixing processes, they can be carried out in the preparation chamber in a predictable manner.

Figure 2:
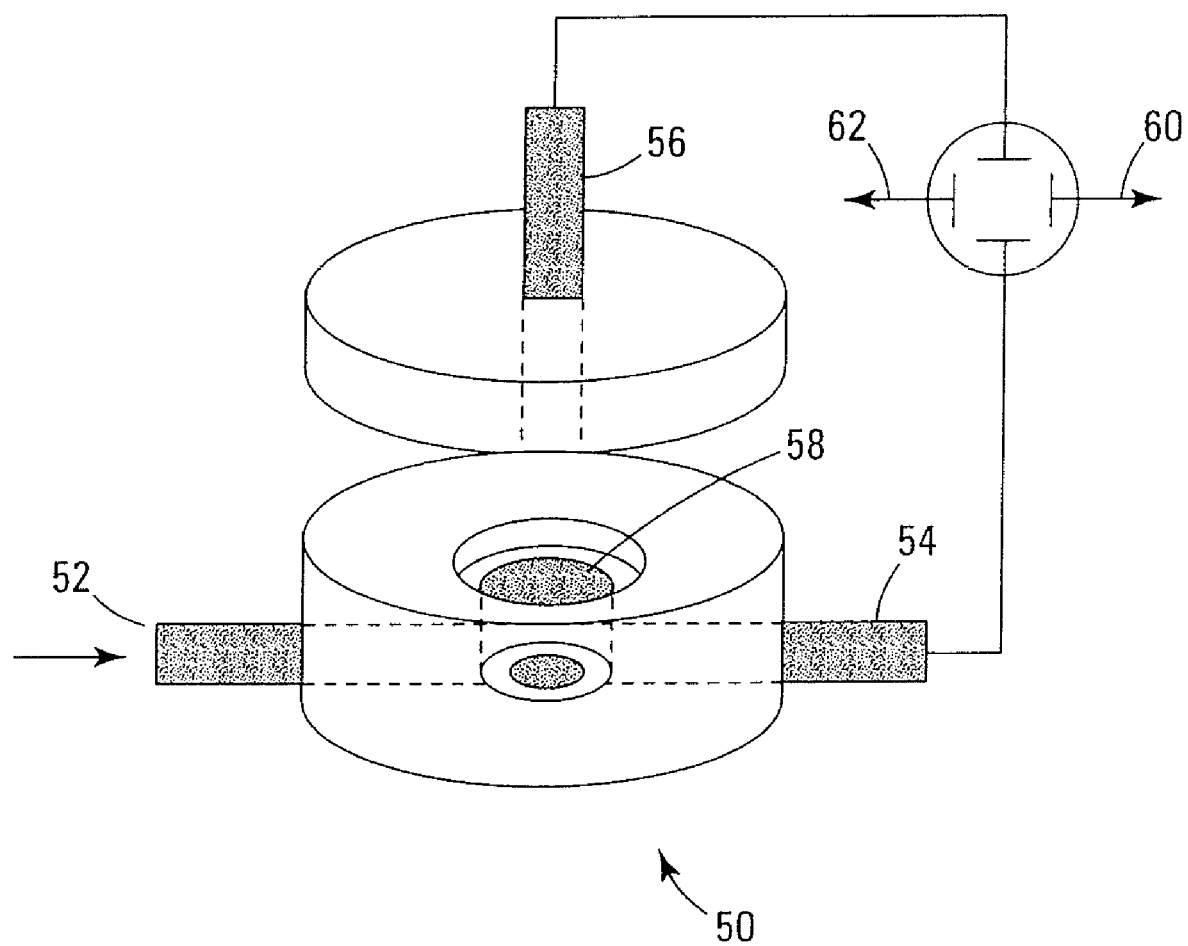
FIG. 2 is an example of a preparation chamber according to the present invention.

FIG. 2 shows one embodiment of a preparation chamber 50. The preparation chamber 50 includes ports 52, 54 and 56. Ports 52 and 54 allow fluids and cell to flow through the chamber. Port 56 is separated from the chamber through a membrane 58 that allows only fluids to pass through. In one example, the membrane 58 is a 0.45 micrometer hydrophilic polyethersulfone membrane (Pall Corporation, Ann Arbor, Mich.) that used with yeast systems. However, the pore size and type of the membrane used may need to be changed depending on the physical properties of a specific cell type. The pore size is typically smaller than the smallest size of a cell.

Port 52 and 54 are connected directly to the chamber, while port 56 is connected to the chamber through membrane 58. Membrane 58 allows fluids to flow through the chamber 50 freely, but cells are retained inside in chamber 50. Cell from the bioreactor are loaded into the chamber 50 by blocking port 56 as the cells and medium from the bioreactor are pumped through the chamber from port 52 to port 54. To perform on-line dilution of cell samples, the appropriate medium is pumped at a known flow rate through the chamber 50 from port 56 into the chamber 50 as cells and medium move through the chamber 50 at a predetermined flow rate for a certain time. To perform on-line staining, port 56 is opened while port 54 is blocked. Staining solutions are then pumped through the chamber 50 from port 56 to port 52, so that cells inside the chamber 50 can be washed and stained. After samples are processed, they are injected into the flow cytometer through outlet 60 for analysis and separation. Waste from the process is expelled through outlet port 62.

Referring again to FIG. 1, while a single preparation chamber 20 is shown in the example, it is understood that one or more of the preparation chambers 20 can be used in the present invention. For example, two or more preparation chambers 20 could be arranged in parallel or in series. Loading of the preparation chambers 20 can then be performed in a timely manner such that by the time the loading of the last preparation chamber of the set of preparation chambers is complete, the sample in the first preparation chamber is ejected and the first preparation chamber is once again ready for loading.

Cells from the preparation chamber 20 then enter the flow cytometer 24. The flow cytometer 24 separates the continuous stream of the heterogeneous population of cells prepared in the preparation chamber 20 into separate subpopulations of cells based on cell characteristics. Flow cytometer 27 can be an optical or an acoustic flow cytometer. In one example, the cells are separated in the flow cytometer 24 based on the staining of the cells. For example, the flow cytometer 24 allows the measurement of forward and side light scatter as well as fluorescence levels of the stained cells.

In one example, the prepared samples are analyzed using a flow cytometer sold under the trade designator FACSCalibur by Becton Dickinson. In FACS (fluorescence-activated cell sorting) flow cytometry, following analysis the sample stream is broken into a series of droplets. Most of those droplets will simply go to the waste collection vessel, but those which contain a cell, or cells, of a user-selected type (e.g., fluorescently labeled cells) will be electrostatically charged and deflected into a sorted fraction container. The flow cytometer 24 can measure the native light scattering properties (e.g., forward and side light scatter) of the cells in addition to any fluorescently labeled cellular constituent. For example, DNA can be labeled directly with a fluorescent dye, and antibodies can be used to label almost any target in a cell.

The flow cytometer 24 is used to select cell subpopulations of interest to be sorted. Sorted cells exit the flow cytometer 24 through outlet ports 44 and 46. In the present example, outlet port 44 is used to remove cells that will not be recycled back to the bioreactor 16. In contrast, the selected cell subpopulation exits the flow cytometer 24 through outlet port 46. The selected cell subpopulation has a cell density that is less than the cell density entering the flow cytometer 24. The selected cell subpopulation moves through the outlet port 46 to the pre-bioreactor preparation chamber 30. The pre-bioreactor preparation chamber 30 prepares the separated subpopulation of cells to be returned to the bioreactor 16. In one example, the separated subpopulation of cells is concentrated (i.e., the cell density is increased) using the chamber 30, where cell media is drawn from the chamber 30 to increase the cell density. The separated subpopulation of cells is then returned to the bioreactor 16, along with fresh media, through the inlet ports 34. For the examples described here, the isolation/enrichment process can start after steady state is reached. However, there can be applications where it may be beneficial to start the isolation/enrichment process before reaching a cell population steady state.

To demonstrate and evaluate bioreactor enrichment with mutant cells through sorting and recycling, a transient mathematical model of the system was developed. The model consists of three ordinary differential equations representing the rate of change of the wild type cell number concentration ($C_n$), the mutants cell number concentration ($C_m$) and the substrate concentration ($C_s$) in the bioreactor. Let F and $F_R$ denote the inlet fresh media and the recycled stream flow rates to the bioreactor, respectively, $C_{mR}$ is the mutants cell number concentration in the recycled stream, V is the reactor volume, $Y_{n/s}$, $Y_{m/s}$, $\mu_{n,max}$, $K_n$, $\mu_{m,max}$ and $K_m$ are the yield coefficients and model parameters for the growth rate expressions of the wild type and mutant cells, respectively. Defining the dilution rate D as F/V, the recycle ratio $\alpha$ as $F_R$/F and the ratio of mutant cells in the recycle stream to those in the bioreactor discharge stream as $\gamma=(F_R C_{mR})/[(F+F_R)C_m]$ the model equations can be written as follows:

$$\frac{dC_n}{dt} = \left(\frac{\mu_{n,max} C_s}{K_n + C_s} - D(1+\alpha)\right) C_n$$

$$\frac{dC_m}{dt} = \left(\frac{\mu_{m,max} C_s}{K_m + C_s} - D(1-\gamma)(1+\alpha)\right) C_m$$

$$\frac{dC_s}{dt} = D(1+\alpha)(C_{sf} - C_s) - \frac{1}{Y_{n/s}} \mu_n C_n - \frac{1}{Y_{m/s}} \mu_m C_m$$

The model equations indicate that coexistence of mutant cells and wild type cells at steady state is only possible if $\gamma=\gamma_c=1-\mu_{m,max}/\mu_{n,max}$. Furthermore, at this single plane in the operating conditions state space an infinite number of steady states are possible. These steady states differ only in the fraction of mutant to wild type cells depending on the initial conditions. At $\gamma$ values higher than $\gamma_c$, the net rate of increase of mutant cells due to growth and recycling is higher than that for the wild type cells due to growth only. Therefore, starting with any fraction of mutant to wild type cells, if $\gamma > \gamma_c$, such that $\gamma$ is greater than $\gamma_c$, the fraction of mutant cells will continue to increase until all the cells in the bioreactor are mutants. On the other hand, at values of $\gamma$ lower than the critical value, the recycling rate of mutant cells is not enough to compensate for the difference in growth rate between the wild type cells and the mutant cells; therefore, mutant cells will eventually vanish in this case.

Figure 3A:
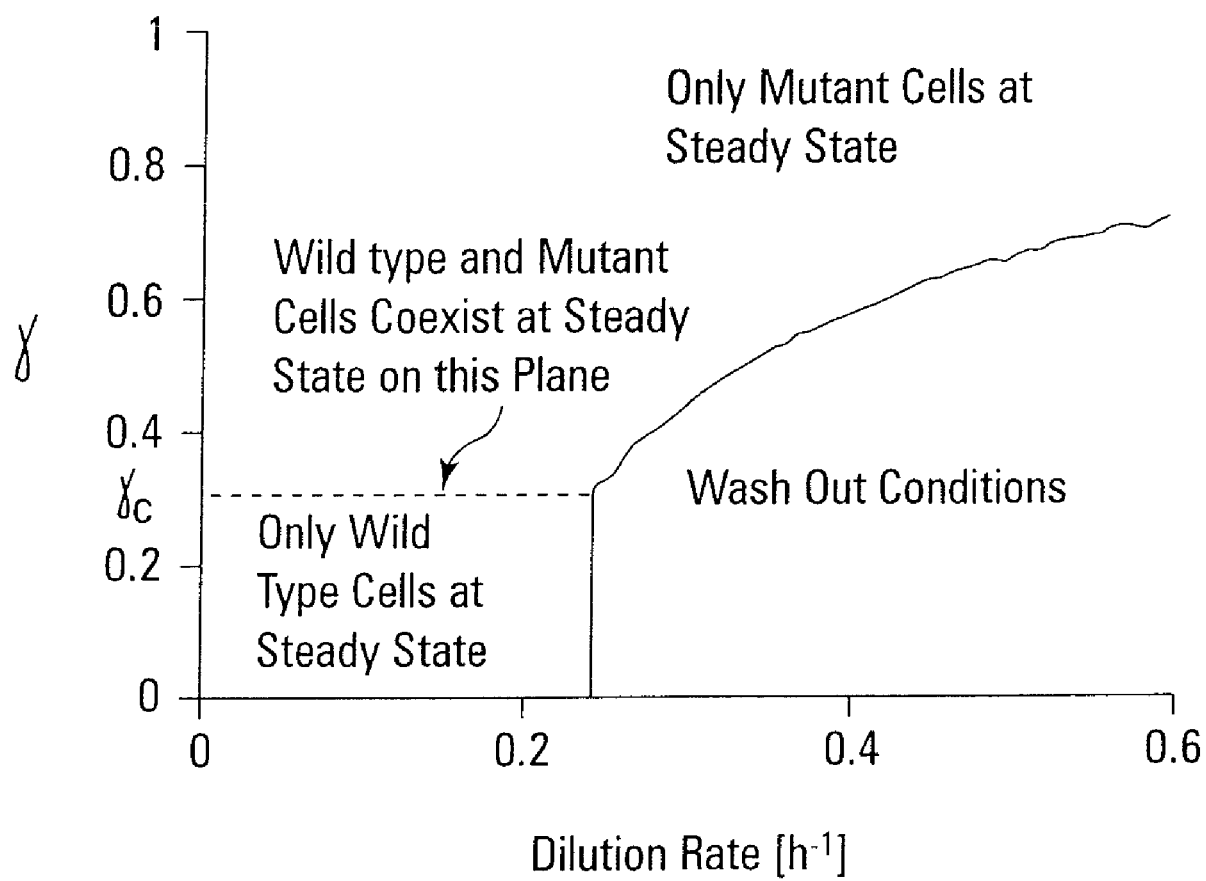
FIG. 3A is an example of an operating diagram for a mutant cells isolation and Recycling System with $\mu_{m,max}=0.7\mu_{m,max}$.
Figure 3B:
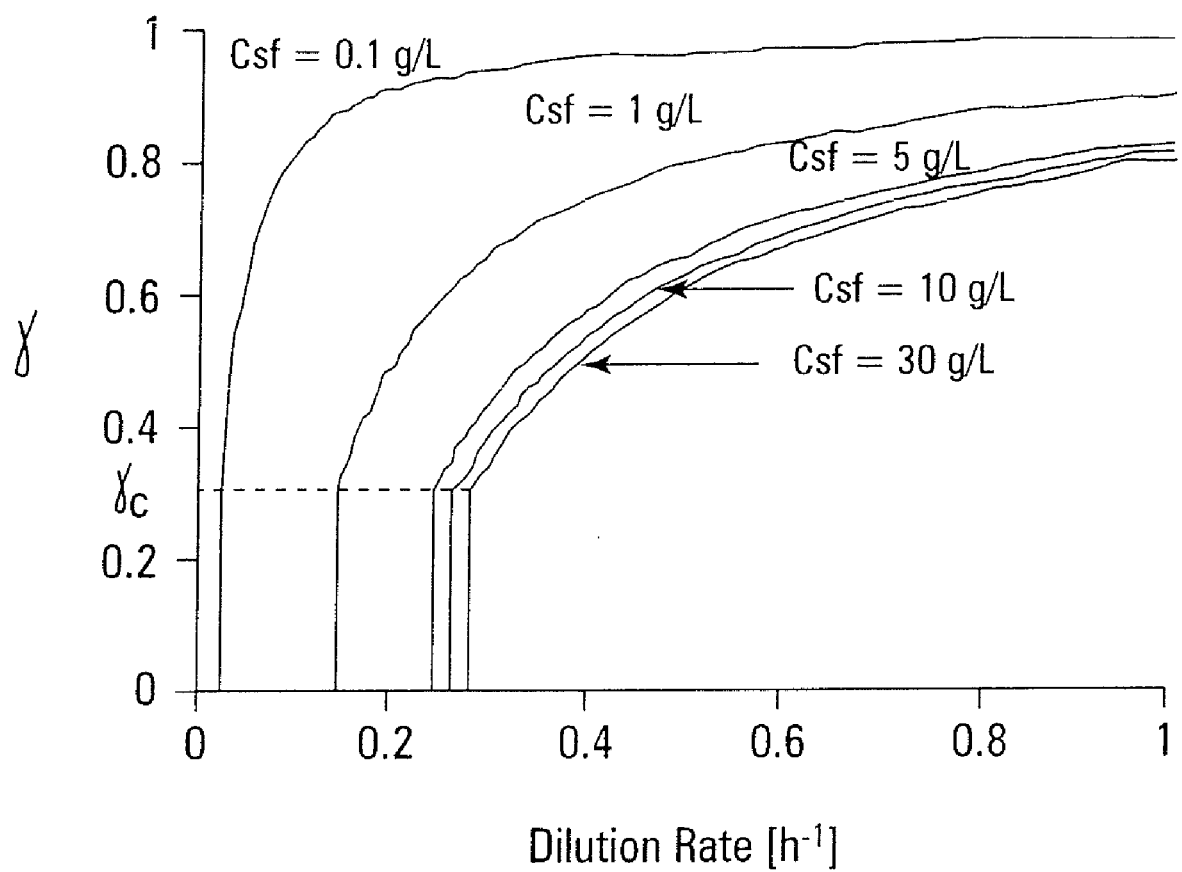
FIG. 3B in an example of the effect of the feed substrate concentration on the operating diagram.

FIG. 3A illustrates the operating diagram of the system in terms of the dilution rate and $\gamma$ at constant substrate feed concentration. Thus, the optimal dilution rate that will allow for the growth of the mutant population can be determined based on the growth characteristics of the mutant and wild type cells. Since the operating conditions depend on the substrate feed concentration, FIG. 3B shows how the operating diagram varies with the feed concentration. As shown in FIG. 3B, the range of dilution rates that can be used decreases with substrate feed.

The capacities of the flow cytometer to analyze and sort cells are limited by the flow conditions and operating parameters of the analytical instrument, which imposes upper limits on the actual value of $\gamma$. The FACSCalibur instrument sold by Becton Dickinson has a maximum sorting rate of 300 cells/sec, however, high-speed sorters are capable of analyzing up to 50,000 cells/sec. Bioreactor enrichment with mutant cells could be achieved faster at higher values of $\gamma$. Furthermore, the steady state mutant cell number concentration is directly proportional to the value of $\gamma$ for a give dilution rate and feed substrate concentration. Hence, in order to minimize the response time of the system, the following procedure is recommended. First the cell number concentration should be reduced by operating at sufficiently low substrate feed concentration such that the discharge rate of cells is below the maximum analysis capacity of the flow cytometer. This would increase the initial value of $\gamma$. To further expedite the process, once the recycling starts, it is recommended to increase the dilution rate to a value higher than the wash out dilution rate of the wild type cells. This, however, would eventually result in a lower steady state cell number concentration of mutant cells. However, once the bioreactor is enriched with mutant cells, lower dilution rate and/or higher substrate feed concentration can be applied to increase the mutant cell number concentration.

Preliminary calculations indicate that following this procedure, the fraction of mutant cells, which grow at 70% of the growth rate of the wild type cells, can increase from $10^{-5}$ to 0.5 within 1-2 days. Further analysis indicate that if the initial discharge rate of cells was kept constant, increasing the dilution rate significantly reduces the system response time, while reducing the bioreactor volume has a minor role in expediting the late system transients and has no effect on the initial transients.

Figure 4A:
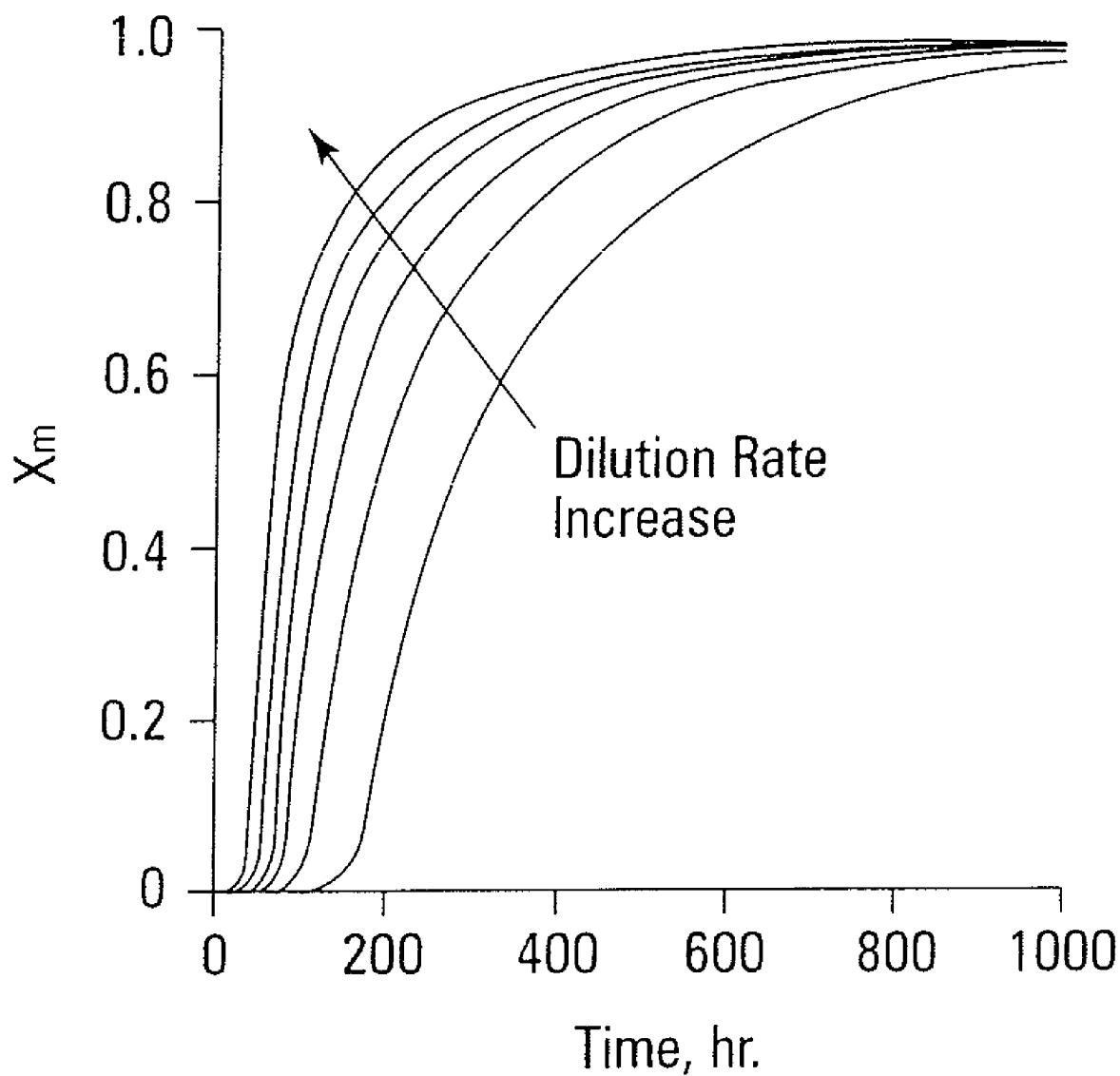
FIG. 4A is an example of the effect of dilution rate on a bioreactor system of the present invention.
Figure 4B:
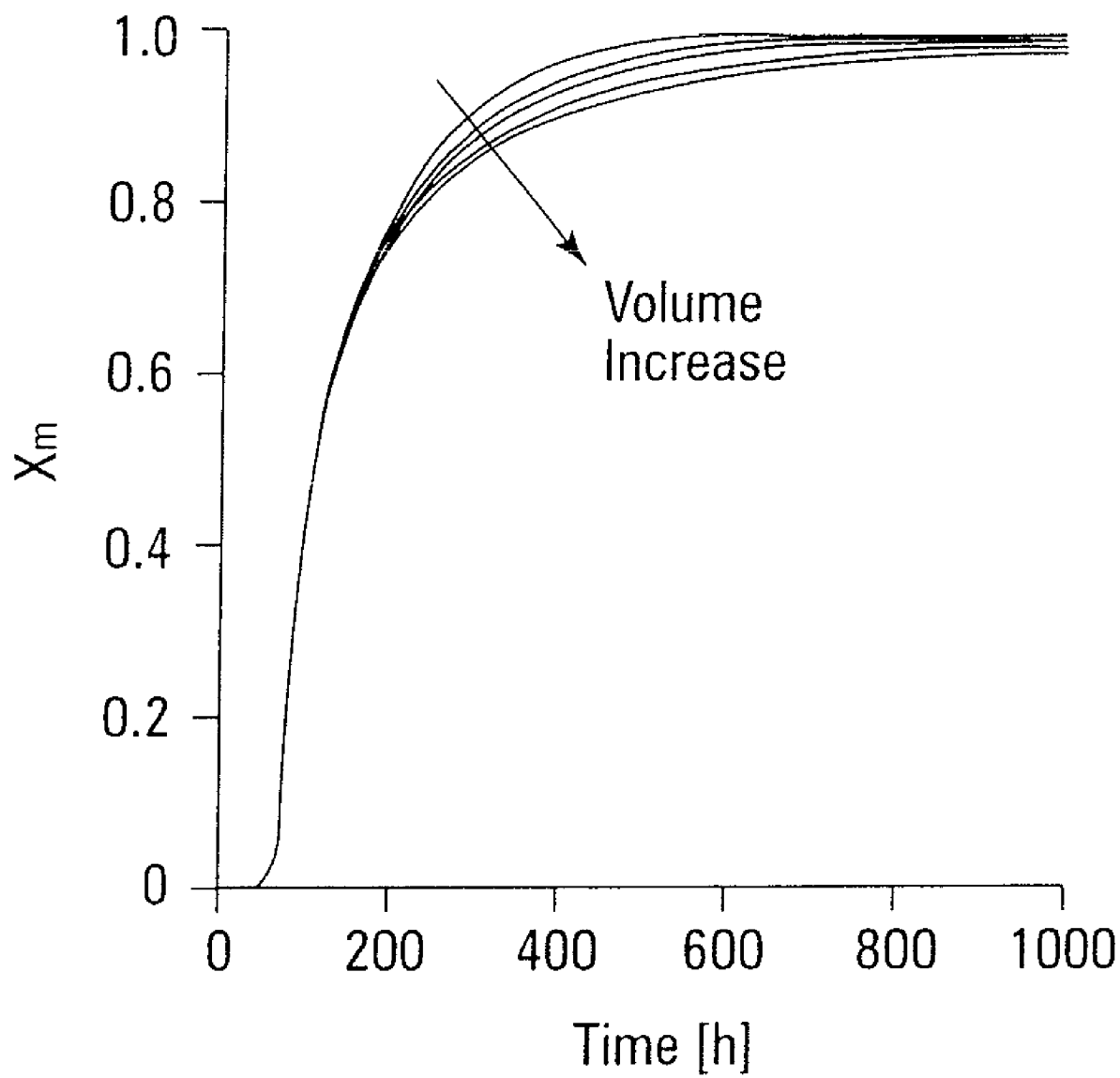
FIG. 4B is an example of the effect of bioreactor volume on a bioreactor system of the present invention.
Figure 4C:
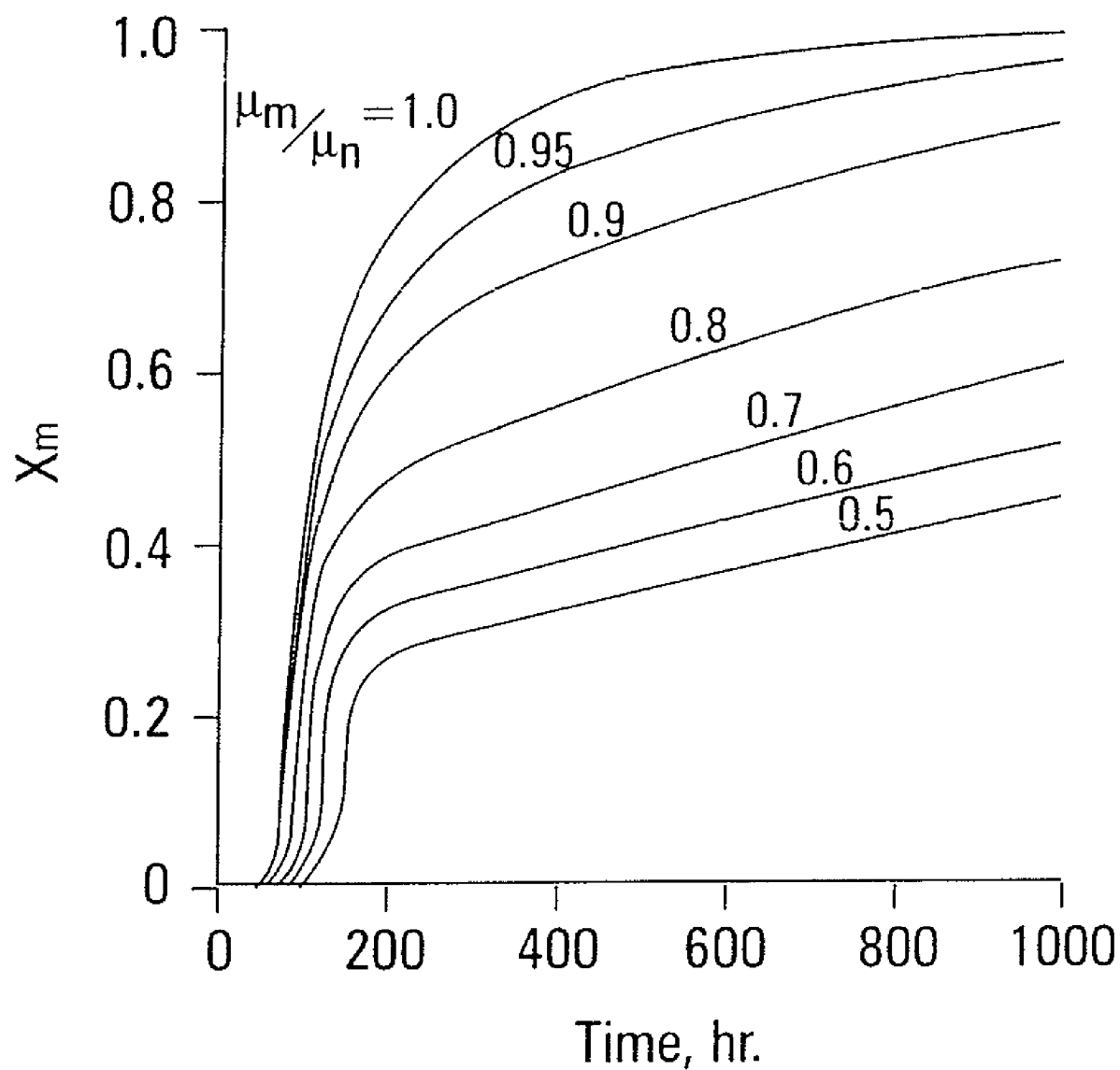
FIG. 4C is an example of the relative growth rate of mutant cells to wild type cells on a bioreactor transient response for mutant cells sorting and recycling.

It was also found that the major factor affecting the system response time is the ratio of the growth rate of mutant cells to the wild type cells. FIGS. 4A, 4B and 4C illustrate the effects of dilution rate, bioreactor volume and the ratio of mutant cells growth rate to that of the wild type cells on the system dynamics in terms of the mutant cells fraction, Xm. FIGS. 4A, 4B, and 4C show how some of the important operating parameters affect the time needed to enrich the mutant population to a desired fraction.

FIG. 4A indicates that if the initial discharge rate of cells was kept constant, increasing the dilution rate significantly decreases the time it takes the system to begin enriching the mutant population. This validates the enriching strategy of the present invention. Furthermore, FIG. 4B shows that reducing the bioreactor volume has no effect on changing the mutant fraction during the early stages of the process, although, it slightly increases the rate of change of the mutant fraction during the latter stages of the process.

It was also found that the major factor affecting the system response time is the ratio of the growth rate of the mutant cells to the wild type cells. FIG. 4C shows that as the growth rate of the mutant cells decreases with respect to the wild type cells, it becomes harder to enrich the mutant population, thus increasing the necessary time of operation.

EXAMPLES

The present invention is illustrated by the following examples. It is to be understood that the particular examples, materials, amounts, and procedures are to be interpreted broadly in accordance with the scope and spirit of the invention as set forth herein.

Example 1

Kinetic Information from Yeast Cultures Expressing GFP

*Saccharomyces cerevisiae* strain YPH399 was transformed with a plasmid expressing green fluorescent protein GFP (2TG1-Gfp(H)) regulated by a TEFI promoter. GFP is a protein that can naturally fluoresce if excited with light of the appropriate wavelength, and therefore, it can be detected using a flow cytometer. While GFP provides only an indirect measure of protein content, it eliminates the need for cell staining.

Figure 5:
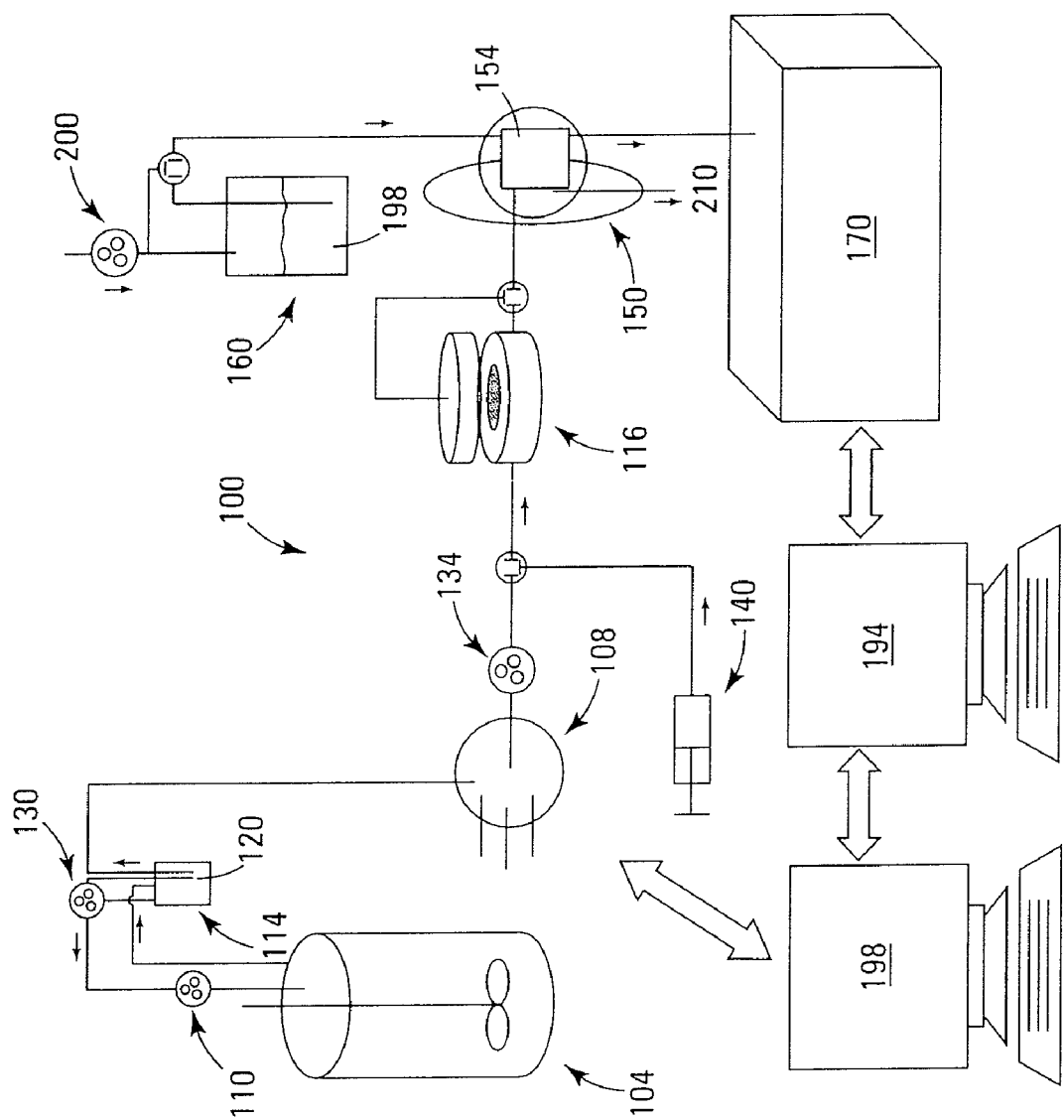
FIG. 5 is an example of a bioreactor system according to the present invention.

The yeast was grown in a bioreactor system 100, shown schematically in FIG. 5, to monitor the dynamics of the cell size distribution, as measured by light scattering properties, and GFP distribution. The forward light scattering properties (as measured by forward scatter, FSC) that correlates with cell size can be used to isolate different sub-populations of cells, and to detect any changes in the physiology of the cells that may affect the size or shape of the population. The GFP fluorescence was monitored together with the FSC and the side scatter signals (correlates with cell density). By sampling the yeast cells frequently (approximately every 18 minutes) throughout the course of the growth experiment, detailed kinetic information about the yeast cell culture was observed.

The 2TG1-Gfp(H) plasmid contained in the yeast cells allowed their growth in media lacking histidine. This provided selective pressure such that only yeast cells containing the plasmid grew. The yeast cells were initially grown in 50 ml of synthetic defined (SD) minimal media lacking histidine to a density of approximately $4.0 \times 10^7$ cells/ml. The yeast cells were then diluted in the bioreactor 104 in fresh SD minimal media to a density of approximately $1.0 \times 10^6$ cells/ml. The culture was maintained at 30 degrees Celsius and mixed using an impeller speed of 800 rpm. The culture pH was controlled at a pH of 4.5.

The bioreactor system 100 used in the present example automates the sample handling and analysis procedures for flow cytometry analysis. The bioreactor system 100 includes a multi-position switching valve 108 (VALCO Instruments Co., Houston, Tex.), the bioreactor 104 (2L bioreactorm, LH Fermentation, Hayward, Calif.), and a first peristaltic pump 110 (Cole-Parmer Instruments Co., Vernon Hills, Ill.) for delivering the yeast cells from the bioreactor 104 to a degassing unit 114 and then back to the bioreactor 104. The degassing unit 114 can be used to ensure that air bubbles from the bioreactor 104 do not enter and become trapped in a preparation chamber 116, discussed below. The multi-position switching valve 108 can be used for adding reagents to and for taking cell samples from the bioreactor system 100.

During degassing, the first peristaltic pump 110 can be used to create a vacuum in an accumulation chamber 120 of the degassing unit 114. The pump 110 continuously pulls the culture from the bottom of the chamber 120 so that the chamber 120 stays essentially empty. Just prior to loading a sample of the culture in to the preparation chamber 116 for processing, the three-way valve 130 is switched so that air is pulled from the head-space of the accumulation chamber 120. This maintains the vacuum and allows the cells to accumulate inside the accumulation chamber 120. Once the proper amount of sample is in the degassing unit 114, cells are pulled through the multi-position valve 108 to allow the sample to proceed to the preparation chamber 116.

A second peristaltic pump 134 can then deliver the degassed yeast culture and reagents added through the multi-position switching valve 108 to the preparation chamber 116 where sample processing can take place. The preparation chamber 116, as described above, permits the cells to be retained in the chamber while other reagents are introduced and/or passed through the chamber. A syringe pump 140 (74900 series, Cole-Parmer Instruments Co., Vernon Hills, Ill.) delivers the precise liquid volumes necessary for diluting the samples of the yeast culture and to deliver the diluted sample of the yeast culture to a sample loop 150. The sample loop 150 provides, in part, a continuous flow loop in which liquid is maintained within the system 100. The sample loop 150 is mounted on a two-way injection valve 154 (Valco Instruments Co., Houston, Tex.) such that after the sample loop 150 has been filled, switching the valve 154 allows a pressure driven mobile phase 160 driven using the pressure regulation system of the flow cytometer 170 to inject the cells into the flow cytometer 170 (FACSCalibure cell sorter, Becton-Dickinson), for analysis. The flow cytometer 170 operates with a standard 488 nm laser having a light output of 15 mW.

The sample loop 150 of the bioreactor system 100 of the present example has a fixed volume. Therefore, counting the cells of the yeast culture sample loaded into the sample loop 150 with the flow cytometer 170 allows the concentration of the yeast culture to be determined. The preparation chamber 116 can be used, as previously discussed, to dilute the yeast culture sample to a desired concentration prior to entering the sample loop 150. In doing this, it is assumed that the preparation chamber 116 behaves as a continuous stirred tank reactor (CSTR), so the yeast culture is well mixed such that the outlet concentration of the yeast culture from the preparation chamber 116 is assumed to be the same as the concentration of the yeast culture in the preparation chamber 116.

Prior to delivering the samples, the preparation chamber and sample loop 150 and the associated lines are all washed thoroughly with citric-buffered saline (CBS) and bovine serum albumin (BSA) solutions. The sample from the bioreactor 104 is then degassed in the degassing unit 114 and passed to the preparation chamber 116, as described above. The cells then need to be diluted to a concentration of approximately $1 \times 10^6$ cells/ml at the preparation chamber 116 prior to being delivered to the sample loop 150. After the sample is loaded, the contents of the sample loop 150 are injected into the flow cytometer 170 for analysis and separation. The sorted cells emerge diluted with sheath solution. At this point it would then be possible to filter, concentrate and/or wash the cells prior to returning them to the bioreactor 104 using a stream of sterile media.

Diluting the yeast culture sample, diluting the cell concentration to approximately $1 \times 10^6$ cells/ml was accomplished using syringe pump 174 at a flow rate of 1.0 ml/min. Once the sample was diluted, it was delivered to the sample loop 150, which is mounted on the two way injection valve 154, via the syringe pump 147. The injection valve 154 was then switched and the yeast sample delivered to the flow cytometer 170.

In the present example, the flow cytometer 170 was a B-D FACSCalibure instrument (Becton-Dickinson Immunocytometry System, San Jose, Calif.). In contrast to its normal operation, in the present system a small metal sheath that is part of the flow cytometer's 170 droplet containment system is removed and the needle that injects the yeast culture sample is joined to the line from the injection valve 154. In addition, under normal operation, a sheath reservoir 198 would need to be depressurized and refilled approximately every 3.5 to 4 hours. Since this would interrupt on-line measurements, a peristaltic pump 200 is used to continuously pump fresh sheath solution at a fixed flow rate into the reservoir 198 such that the level of the reservoir 198 does not change and the pressure is maintained at the normal value of 4.5 psi. Spent sheath was drained from a hole in the waste reservoir 210.

The pumps and valves of the bioreactor system 100 were controlled by a personal computer 194 equipped with a DT302 data acquisition card (Data Translation, Inc. Marlboro, Mass.) through digital I/O and D/A ports. TestPoint software development toolbox (Capital Equipment Corporation, Billerica, Mass.) was used to develop Windows based data acquisition and control software to direct the operation of all the components of the bioreactor system 100. QuicKeys software (CE Software, West Des Moines, Iowa) was used to control Cell Quest software (Becton Dickinson, San Jose, Calif.) on a Macintosh computer 198 for data acquisition from the flow cytometer 170. Timing of all the operations of the bioreactor system 100 were controlled by the personal computer 194. Communication between the Macintosh computer 198 and the personal computer 194 was implemented using DAVE file transfer software (Thursby Sortware, Arlington, Tex.).

Control of cell sample dilution in the preparation chamber 116 prior to being delivered to the sample loop 150 can be accomplished was accomplished according to the following dilution model. During the dilution process at the preparation chamber 116, the concentration of the yeast cell into the sample loop is zero, and the inlet and outlet flow rates are equal. Therefore, the concentration of cells within the chamber at any point in time (and thus, the outlet concentration) are given by:

$$C(t_D) = C_0 \cdot e^{-D \cdot t_D} \qquad (1)$$

Where $C(t_D)$ is the concentration of cells in the preparation chamber 124 as a function of dilution time, $t_D$, $C_o$ is the initial concentration of cells in the preparation chamber 116, and D is the dilution rate in the chamber (time$^{-1}$). The dilution rate is defined as the flow rate divided by the chamber volume. Given this, the concentration profile of the cells in the sample loop 150 after the preparation chamber 116 as a function of dilution time and position, l (length), in the tubing. This is described by equation 2, where A is the cross sectional area of tubing and F if the volumetric flow rate.

$$C(t_D, l) = C_0 \cdot e^{-D\left(t_D - \frac{l \cdot A}{F}\right)} \quad (2)$$

The total number of cells in the sample loop 150, N, at any given time for a particular flow rate can be found by integrating the concentration profile over the length of the tubing that corresponds to the sample loop 150, between positions $l_1$ and $l_2$ and is given by:

$$N = \int_{l_1}^{l_2} A \cdot C_0 \cdot e^{-D\left(t_D - \frac{A \cdot l}{F}\right)} dl \quad (3)$$

Thus, the initial concentration of cells in the preparation chamber 116, $C_o$, can be determined since all the variables are set by the system 100 and N is the number of events counted by the flow cytometer 170. The initial concentration of cells in the preparation chamber 116 can then be determined using the relationship:

$$C_0 = \frac{N \cdot D}{F}\left[e^{-D\left(t_D - \frac{A \cdot l_2}{F}\right)} - e^{-D\left(t_D - \frac{A \cdot l_1}{F}\right)}\right]^{-1} \quad (4)$$

Once the cell concentration is known, the dilution time, $t_D$, can be adjusted such that a desired number of events, N, will be detected in the flow cytometer 170. Thus, the amount of dilution required for a sample can be approximated by the concentration of the cell determined from the previous measurement.

After each sample was analyzed, a statistical file was created in the CELLQuest software that could be read by the personal computer 194 on a drive shared with the Macintosh computer 198. Dilution of the samples within the preparation chamber 116 was controlled automatically by a subroutine executing on the personal computer 194. A sample concentration of $1 \times 10^6$ cells/ml was determined to yield a count of approximately 100,000 events on the flow cytometer 170 and a maximum analysis rate of 1000 events/sec. Therefore, the computer 194 was programmed in such a way that when a sample yields a count of greater than 100,000 events on the flow cytometer 170, the next sample was diluted by a sufficient amount as determined by equation (1), so that the next sample would yield a count of approximately 100,000 cells in the sample loop 150. Dilution limits were set for each sample to prevent errant samples from irreversibly increasing the dilution factor by large amounts.

Throughout the exponential growth phase of a culture, the increase in the concentration of cells was given by the known expression:

$$C_R(t_c) = C_{R0} \cdot e^{\mu \cdot t_c} \quad (5)$$

Where $C_R(t)$ is the cell concentration of the culture at time, $t_c$, $C_{RO}$ is the initial concentration of cells in the bioreactor 104, and $\mu$ is the specific growth rate (time$^{-1}$). Given that the concentration of cells in the bioreactor 104 at any time, $C_R(t_c)$, is equal to the concentration of cells in the preparation chamber 124 prior to dilution, $C_o$, equations (1) and (5) can be related to each other to yield:

$$C_{R0} \cdot e^{\mu \cdot t_c} = C(t_D) \cdot e^{D \cdot t_D} \quad (6)$$

Solving for the dilution time gives the following relation between the dilution time and the total culture time:

$$t_D = \frac{\mu}{D} \cdot t_c - \frac{1}{D} \cdot \ln\left(\frac{C(t_D)}{C_{R0}}\right) \quad (7)$$

Thus, the specific growth rate of the culture can be determined from the slope of a plot of the dilution time, $t_D$ versus the total culture time, $t_c$.

In this example, the on-line dilution and counting capabilities of the system 100 were tested and confirmed by monitoring the growth of a yeast culture in a batch bioreactor. On-line count measurements were taken approximately every 18 minutes, while off-line measurements using an Elzone particle counter were taken every hour. The Elzone particle counter operates according to the Coulter principle. In this method a defined volume of the cell suspension flows through a small orifice of a glass probe that is subjected to an electric field between outside and inside of the probe. Particles that flow through the orifice cause discrete resistance changes that are detected and counted.

Figure 6A:
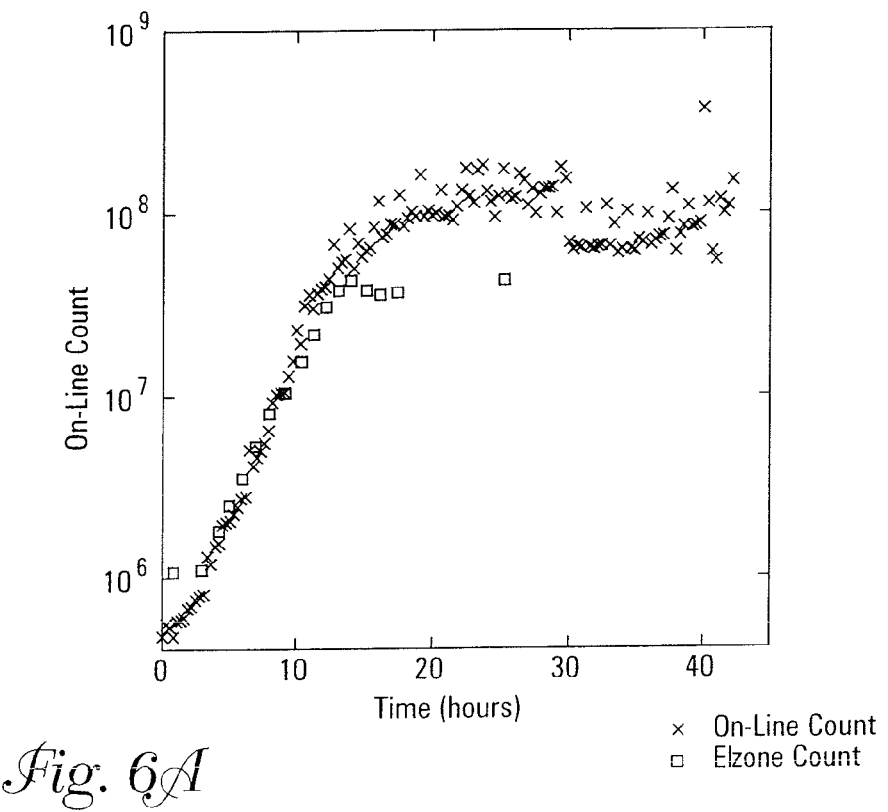
FIG. 6A is an example of a growth curve determined by on-line and off-line counts of a yeast cell culture from the bioreactor system of FIG. 5.

The on-line and off-line counts were used to construct the growth curve of the culture and this is plotted in FIG. 6A. FIG. 6A shows that the on-line cell counts were larger than the corresponding off-line cell counts. One factor that may contribute to the higher on-line counts was fouling of the membrane in the preparation chamber 116 over the course of the experiment. The membrane in the preparation chamber 116 was changed after 30 hours of continuous operation. FIG. 6A shows that this resulted in an immediate 50 percent decrease in the on-line cell counts. A second factor that may contribute to the higher on-line cell counts could be the excessive dilution times required as the culture reaches higher cell densities. The error in the calculated cell concentration due to any inaccuracies in the flow cytometery counts increases exponentially with an increase in the dilution time according to equation 4.

Figure 6B:
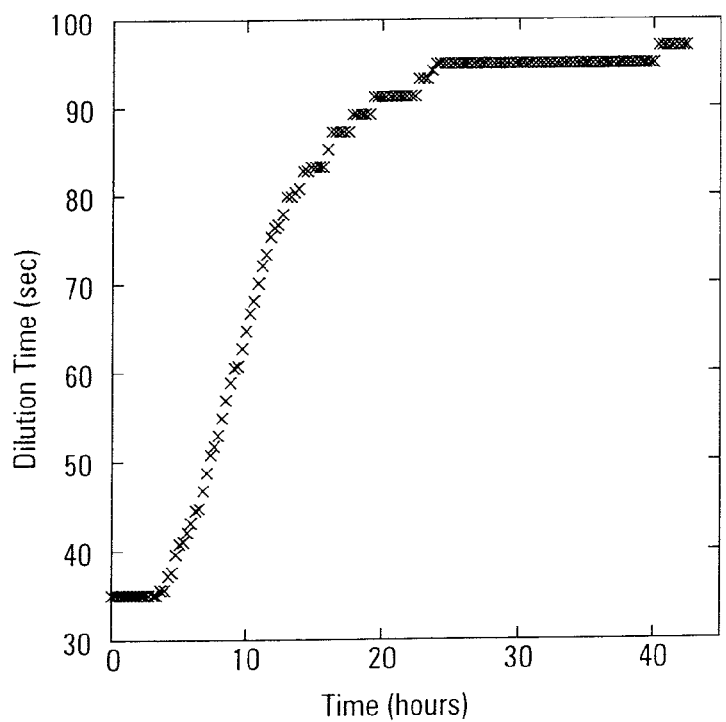
FIG. 6B is an example of dilution time for yeast cell culture samples from the bioreactor system of FIG. 5.

As the cell culture grew in cell number during the course of the experiment, it was necessary to dilute the sample to a concentration suitable for flow cytometry analysis. A cell concentration of approximately $1 \times 10^6$ cells/ml was found to be ideal, since it resulted in a maximum event rate of no more than 1000 cells/sec. Higher cell concentrations would result in higher analysis rates, which in turn increases the likelihood of two or more cells being analyzed simultaneously. The amount of dilution required throughout the experiment is shown in FIG. 6B. Dilution did not start until the cells entered the exponential growth phase, where it steadily increased until the cells reached the stationary phase.

Figure 7A:
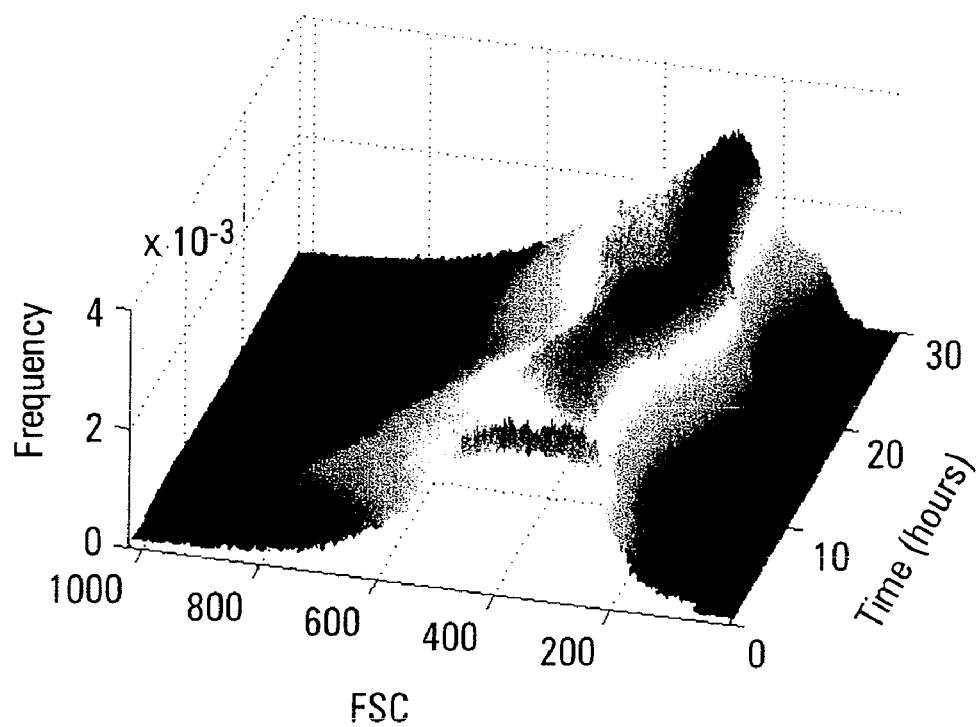
FIG. 7A is an example of a forward scatter (FSC) distribution plotted as a function of culture time for yeast cells grown in the bioreactor system of FIG. 5.
Figure 7B:
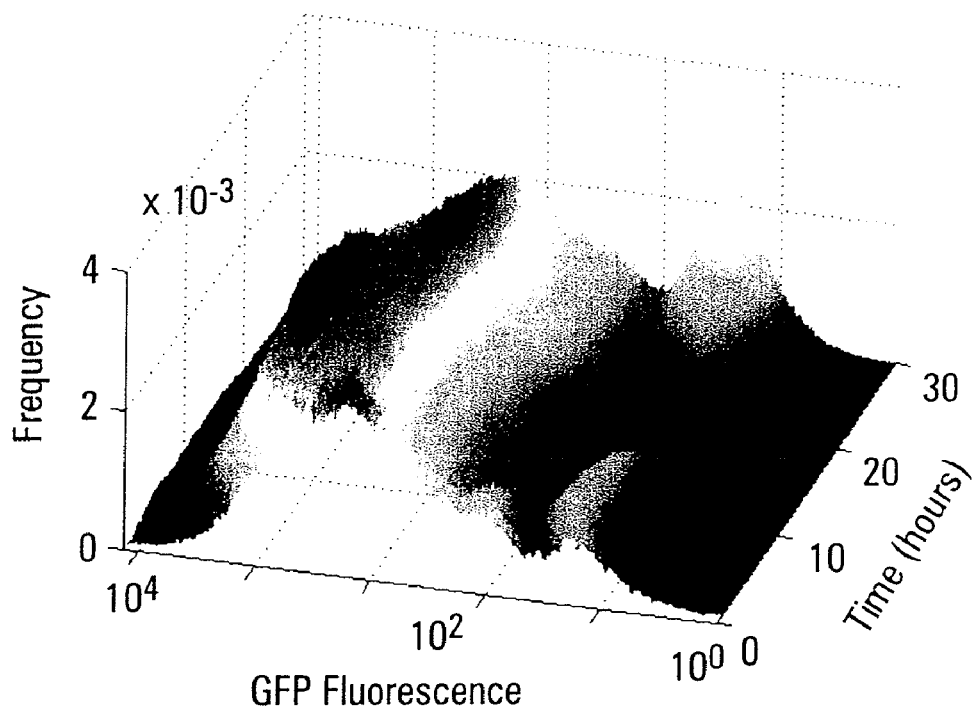
FIG. 7B is an example of a green fluorescent protein (GFP) fluorescence distribution plotted as a function of culture time for yeast cells grown in the bioreactor system of FIG. 5.

The dynamics of the yeast culture cell size distribution and directed isolation through the use of the GFP fluorescence was shown to be possible with the bioreactor system 100 of the present example. The dynamics of the cell size distribution of the FSC signal are shown as a 3-D plot in FIG. 7A depicting the time variations in the FSC properties of the population. Similarly, FIG. 7B shows the time evolution of GFP expression and translation.

Although no quantitative data can be extracted from the FSC data, important information about the state of the culture can be inferred by the changes that occur throughout the experiment. The culture has been inoculated with a fairly uniform population of cells. However, by the end of the lag phase the FSC of the population became more distributed. After the slight increase in the FSC signal that accompanied the beginning of the exponential growth phase, the signal lowered slightly and the population remained uniform until the late exponential phase. After approximately 12 hours, a new, slightly smaller population of cells emerged.

Example 2

Sorting of Polymer Beads Based on Fluorescence

Polymer beads (polymethacrylate microspheres) having a diameter of approximately 2.0 µm, were used to in further testing the sorting and separation capabilities of the bioreactor system 100 described above. The polymer beads of the present example either did, or did not, included fluorescent markers. Non-fluorescent marked beads were supplied from Duke Scientific Corporation, Palo Alto, Calif. Fluorescent marked beads, labeled with FITC (fluoresceinisothiocyanate), were supplied by Becton Dickson (San Jose, Calif.), and sold under the trade designator Calibrite. The sorting ability of the system 100 was then tested by sorting and separating the fluorescent and the non-fluorescent beads using the flow cytometer 170 portion of the system 100.

Fluorescent and non-fluorescent beads were mixed in a ratio of approximately 40:60 by number of fluorescent to non-fluorescent beads. The beads were suspended to a concentration of approximately $1.0 \times 10^6$ beads/ml in a 1% solution of SDS to prevent clumping of the beads. The flow rate used for separation by the flow cytometer 170 was approximately 1000 beads/sec.

Figure 8A:
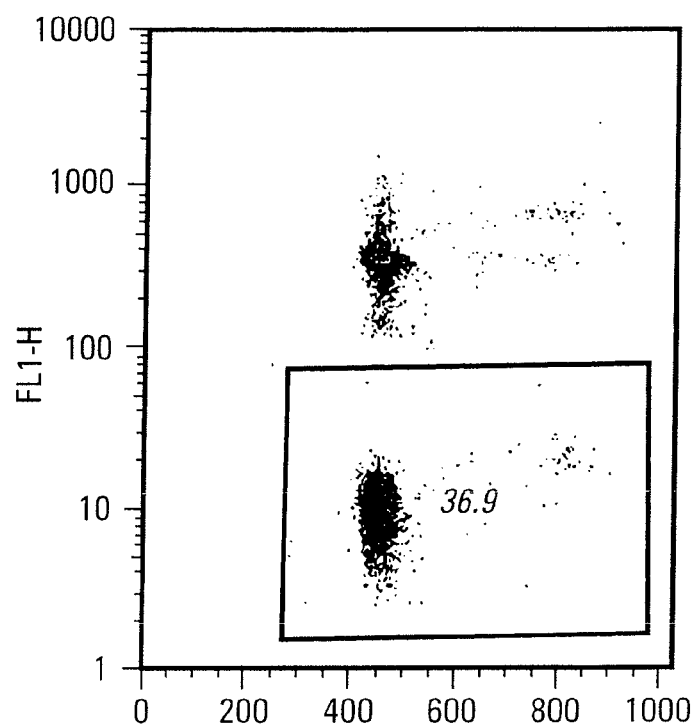
FIG. 8A is an example of a distribution of fluorescent polymer beads prior to sorting based on a predetermined-gate in the bioreactor system of FIG. 5.

The unsorted population of beads is shown in FIG. 8A. The x-axis of FIG. 8A is the forward scatter (FSC), indicating size and the y-axis is green fluorescence. Thus, the unsorted population has two population of beads, fluorescent and non-fluorescent. A gate was drawn around the non-fluorescent bead population, FIG. 8A, and the beads were sorted based on that gate. The gate can be used to limit certain measured properties of the beads to a certain range. Because in the present example two properties have been measured (fluorescence and light scattering reflecting cell size) the property space is two dimensional and can be represented by an area. The gate defines a subsection of this area. For instance, if the bead has properties that fall in this gate the sorting process can be triggered. The gate can be set-up by the instrument software of the system 100 that controls data acquisition and cell sorting.

Figure 8B:
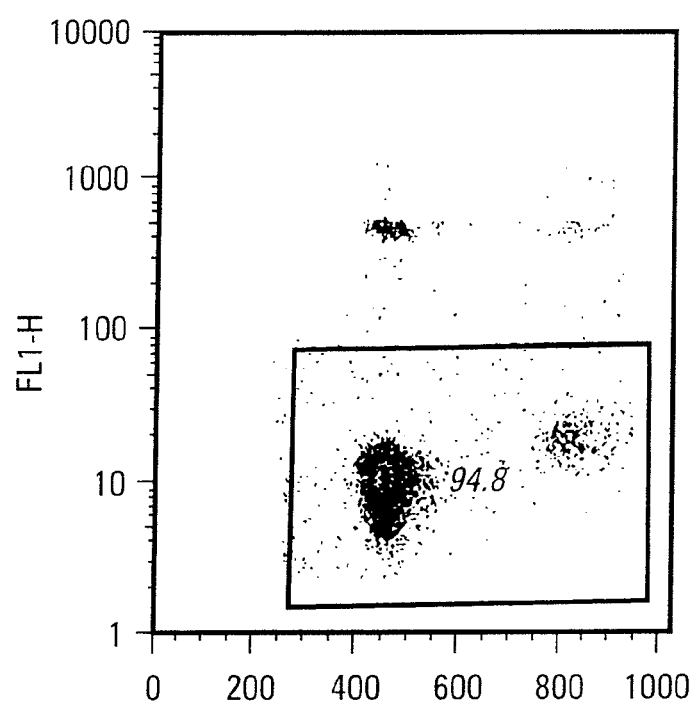
FIG. 8B is an example of the distribution of fluorescent polymer beads of FIG. 8A having been sorted in the bioreactor system of FIG. 5 based on the predetermined gate.

The sorted bead solution from the flow cytometer were then centrifuged at 4500 rpm for 20 minutes. The beads where then resuspended in 1 ml of double distilled water and reanalyzed on the flow cytometer. The results are illustrated in FIG. 8B, which shows an enrichment in the population of the beads inside the area of the gate. The percentage of beads inside the gate increased from 36.9% to 94.8%.

Example 3

Reproducibility of Sorting System

The ability of the bioreactor system 100, described above, to produce reliably reproducible separation results was also tested. In testing the reproducibility of the system 100, a bead suspension was loaded into the preparation chamber 124 via the pump 134. The bead suspension had a concentration of approximately $1.0 \times 10^6$ beads/ml in a 1% solution of SDS to prevent clumping of the beads. The flow rate used for the tests was approximately 1000 beads/sec. The beads were 2.0 µm polymethacrylate microspheres supplied from Duke Scientific Corporation (Palo Alto, Calif.). The beads were washed with PBS, and loaded into the sample loop 150 via the syringe pump 174 (1.0 ml/min) for 35 seconds. This was repeated eight (8) times over a period of several hours and the FSC distributions were analyzed in each case. The average FSC for all the samples was 240.1 (relative units) with a standard deviation of 0.72 indicating a high reproducibility. Likewise, the average percentage coefficient of variation (CV) for all the samples is 5.89 with a standard deviation of 0.12. It is evident that both the mean FSC and percentage CV for each of the samples is very stable. By comparison, a bead sample run manually on the flow cytometer 170 yielded a mean FSC measurement of 237.91, which is in close agreement with the on-line measurements. Furthermore, the % CV on medium flow rate (36 µl/min) and low flow rate (12 µl/min) settings is 10.81 and 4.23 respectively. This suggests that the flow rate of the sample stream during on-line measurements is between the medium and low flow rate settings of the instrument.

Example 4

Sorting of Fluorescent Yeast Population

A population of yeast (YPH399a:pTef1-Timer) expressing the E5 mutant of drFP583 protein ("Fluorescent Timer") was used to further test the sorting and separation capabilities of the bioreactor system 100 described above. The yeast used in the present example include drFP583, which is a fluorescent protein is initially green but changes with time to red fluorescence. The yeast culture was incubated as described above for 3 days, hence the fluorescent protein in the yeast cells would fluoresce red.

Figure 9A:
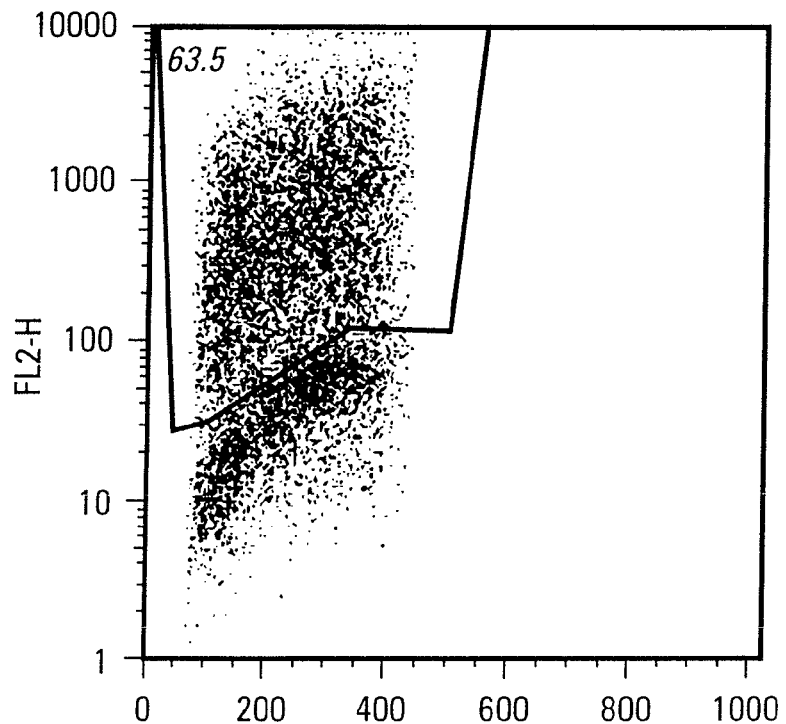
FIG. 9A is an example of a distribution of fluorescent yeast cells prior to sorting based on a predetermined gate in the bioreactor system of FIG. 5.
Figure 9B:
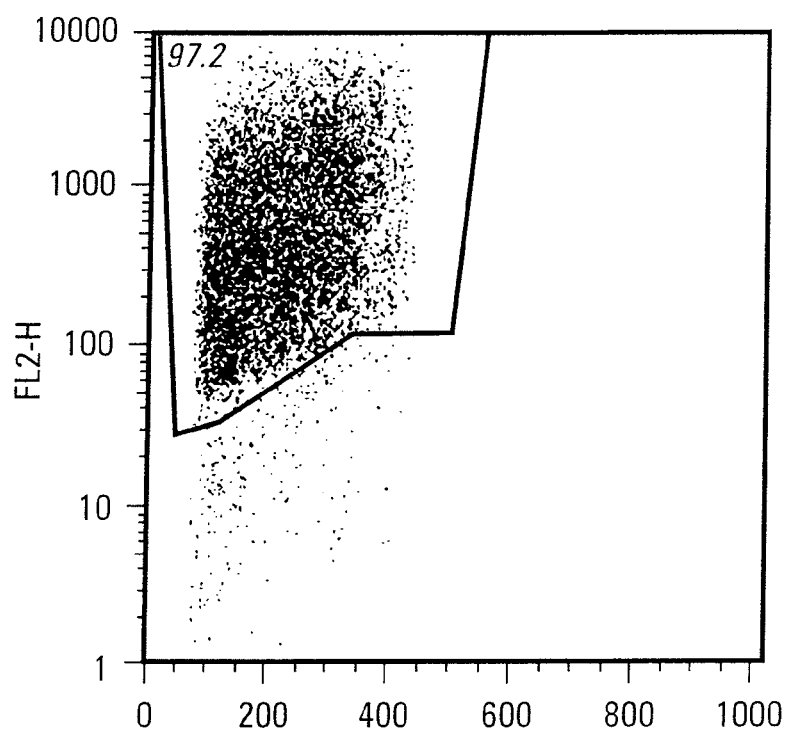
FIG. 9B is an example of the distribution of fluorescent yeast cells of FIG. 9A having been sorted in the bioreactor system of FIG. 5 based on the predetermined gate.

FIG. 9A shows the yeast cell population before sorting in the flow cytometer 170. As FIG. 9A shows, there are two populations of cells, red fluorescent cells (about 65%) and non-fluorescent cells. A gate was drawn around the fluorescent cells and the cells were sorted in the flow cytometer 170 based on this gate. The concentration of the cells initially was $10^7$ cells/ml and the cytometer was operated on low flow rate so as to provide an event rate close to 2000 events/sec. The sorted cells were then centrifuged at 4500 rpm for 20 minutes and resuspended in 1 ml of sterile double distilled water. The separated yeast cells were then re-analyzed on the cytometer 170. The results are illustrated in FIG. 9B, which shows an enrichment in the population of the fluorescent yeast cells inside the area of the gate. In the sorted cell preparation 97.2% of the cells are fluorescent as opposed to 63.5% in the original population.

Example 5

Sorting of Non-Fluorescent Yeast Based on Size

Figure 10A:
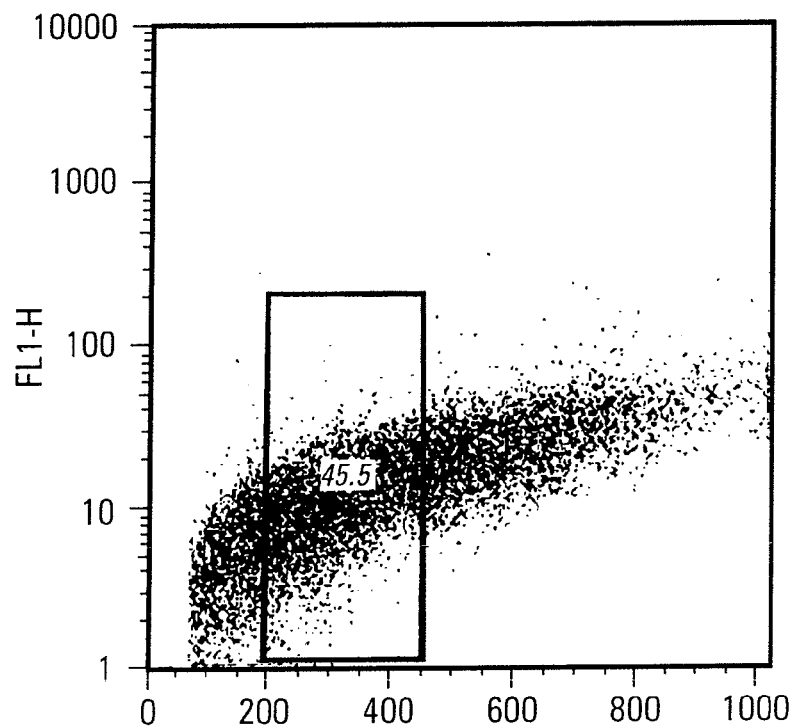
FIG. 10A is an example of a distribution of yeast cells prior to sorting based on size in the bioreactor system of FIG. 5.

A population of yeast cells (YPH399) were used to test the sorting and separation capabilities of the bioreactor system 100 described above based on the forward scatter parameter, which is an indicator of cell size. The unsorted population of yeast cells is illustrated in FIG. 10A. A gate was drawn so as to select about 45% of the yeast cell population. The yeast cells were then sorted based on this gate using the flow cytometer 170 of bioreactor system 100. The flow cytometer 170 was operated at a low flow rate setting, which resulted in an analysis rate of approximately 1000 cells/sec for a cell concentration of approximately $1 \times 10^6$ cells/ml.

Figure 10B:
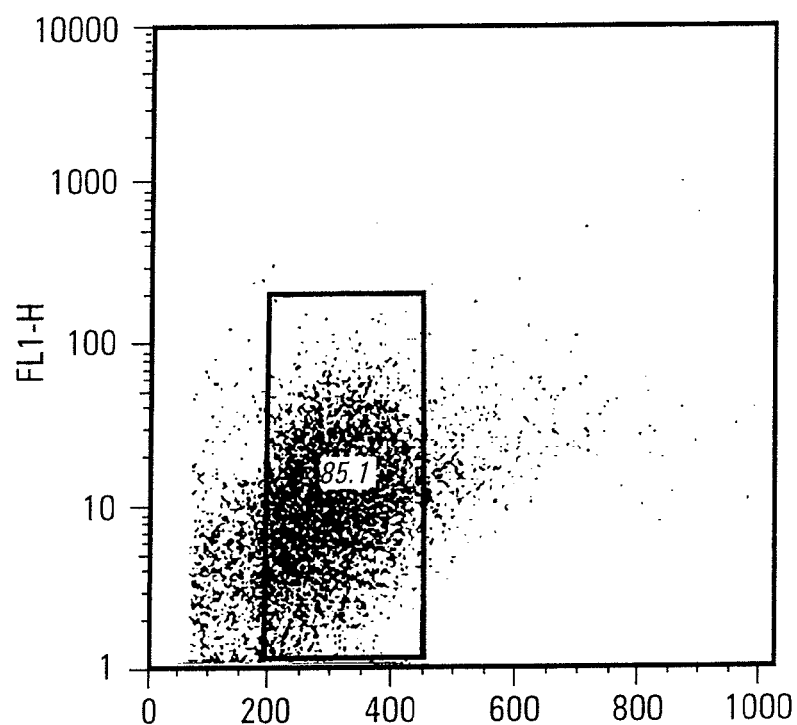
FIG. 10B is an example of the distribution of yeast cells after being sorted based on size in the bioreactor system of FIG. 5.

The sorted cells were then centrifuged at 4500 rpm for 20 minutes and resuspended in 1 ml of sterile double distilled water. The separated yeast cells were then re-analyzed on the cytometer 170. The results are illustrated in FIG. 10B, which shows an enrichment in the population of the cell size defined by the area of the gate. In the sorted cell preparation 85% of the sorted cells fell in the sorting gate which illustrates enrichment compared to the initial population.

Example 6

Chemostat Monitored with Bioreactor System

Sacchromyces cerevisiae strain YPH 399a containing the 2 μm plasmid for the expression of GFP, as described above, was used in the present example to examine the dynamics of a chemostat containing the yeast. The transient behavior of the fluorescence, light scattering, and cell number concentration were monitored using the bioreactor system 100.

SD minimal media was used containing various amounts of glucose, 0.67% weight/volume of Difco yeast nitrogen base, 100 mg/L of adenine sulfate, 60 mg/L uf uracil, 20 mg/L of L-tryptophan, 50 mg/L of leucine, and 150 mg/L of L-lysine-HCl. The media was buffered at a pH of 4.5 by the addition of citric acid and sodium citrate. Selective pressure was applied to the culture by omitting histidine from the media.

The bioreactor 104 was operated in batch mode with the media containing 9.8 g/L of glucose, which was the limiting nutrient. Thirteen (13) hours after inoculation, the feed and exit pumps were turned on, and the reactor 104 began operation as a chemostat (a completely controlled experimental system for testing microbial growth and competition). The reactor volume was maintained at approximately 450 ml.

Initially, the glucose feed contained 6.6 g/l and a dilution rate of 0.22 $hr^{-1}$ was used. After operating at these conditions for nine (9) hours, the dilution rate was increased to 0.35 $hr^{-1}$ and the glucose concentration was lowered to 5.0 g/L. The reactor 104 was kept at these conditions for 3.5 hours at which point the dilution rate was dropped back to 0.22 $hr^{-1}$. The reactor was kept at these conditions for 16.25 hours. At this point the glucose concentration of the media was dropped to 2.5 g/L. After 1 hour the dilution rate was dropped to 0.091 $hr^{-1}$. In order to measure the fluorescence and light scattering properties, the chemostat was hooked up to the bioreactor system 100 described above. The on-line cells counts were compared to the off-line counts obtained from an Elzone particle counter.

Figure 11:
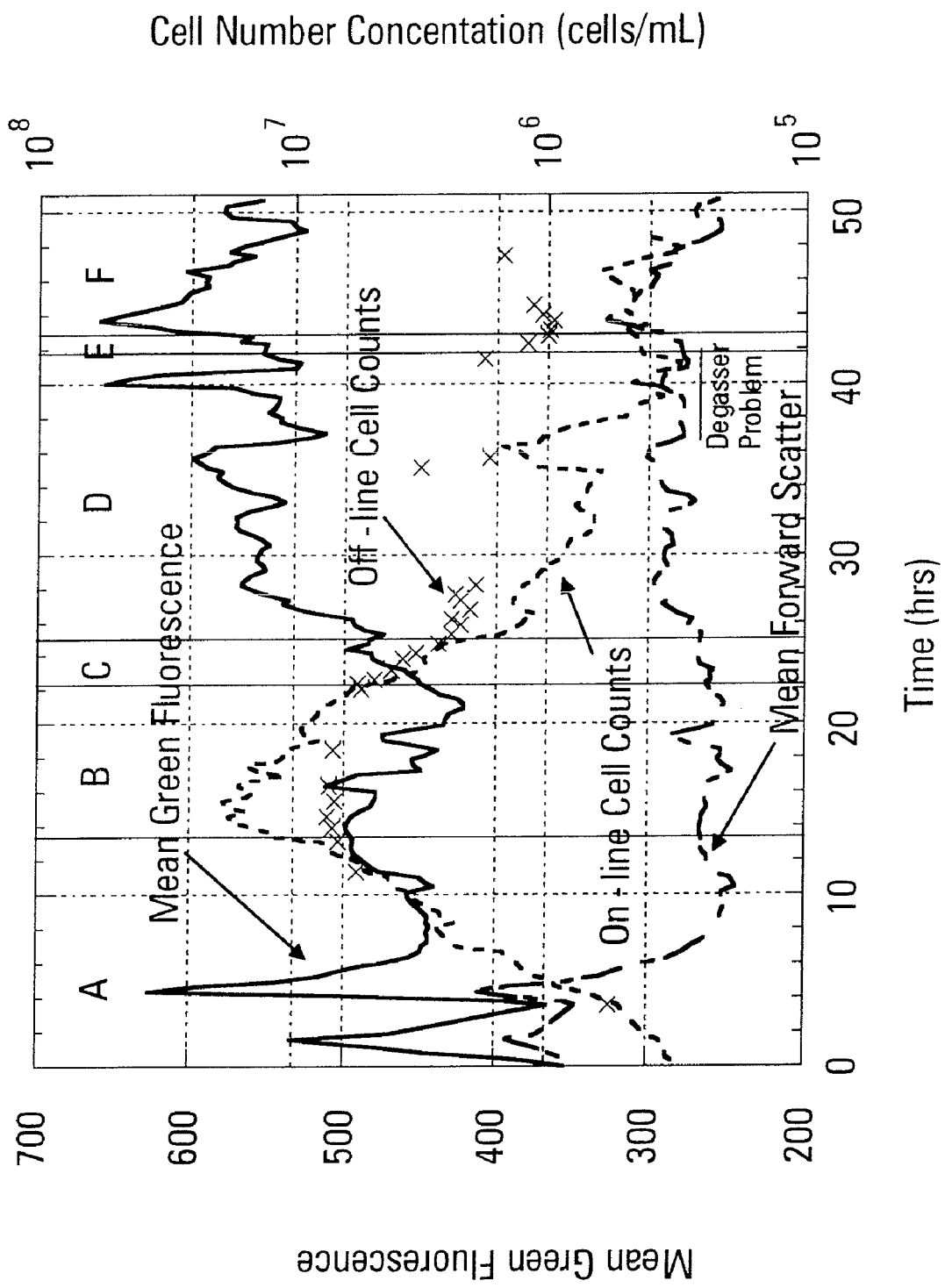
FIG. 11 is an example of a number density and average fluorescence and light scattering properties of cells in the bioreactor system of FIG. 5.
Figure 12A:
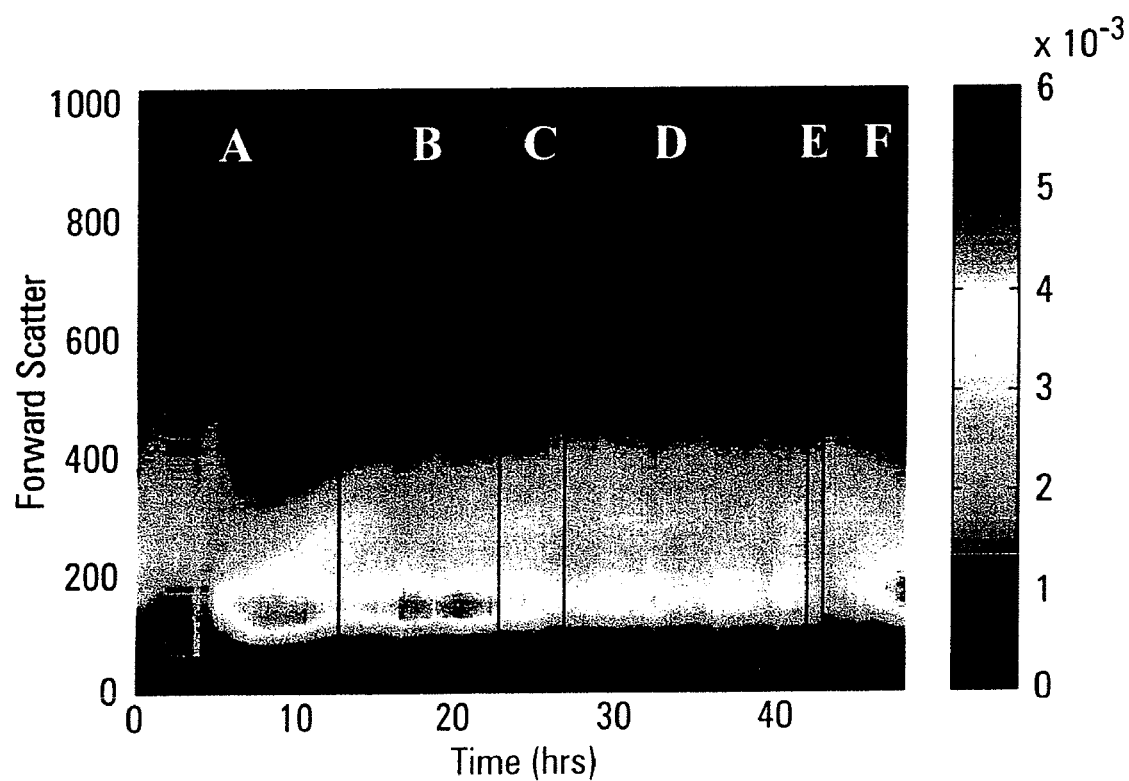
FIG. 12A is an example of a time profile for forward scatter (cell size) of the yeast cells data of FIG. 11.
Figure 12B:
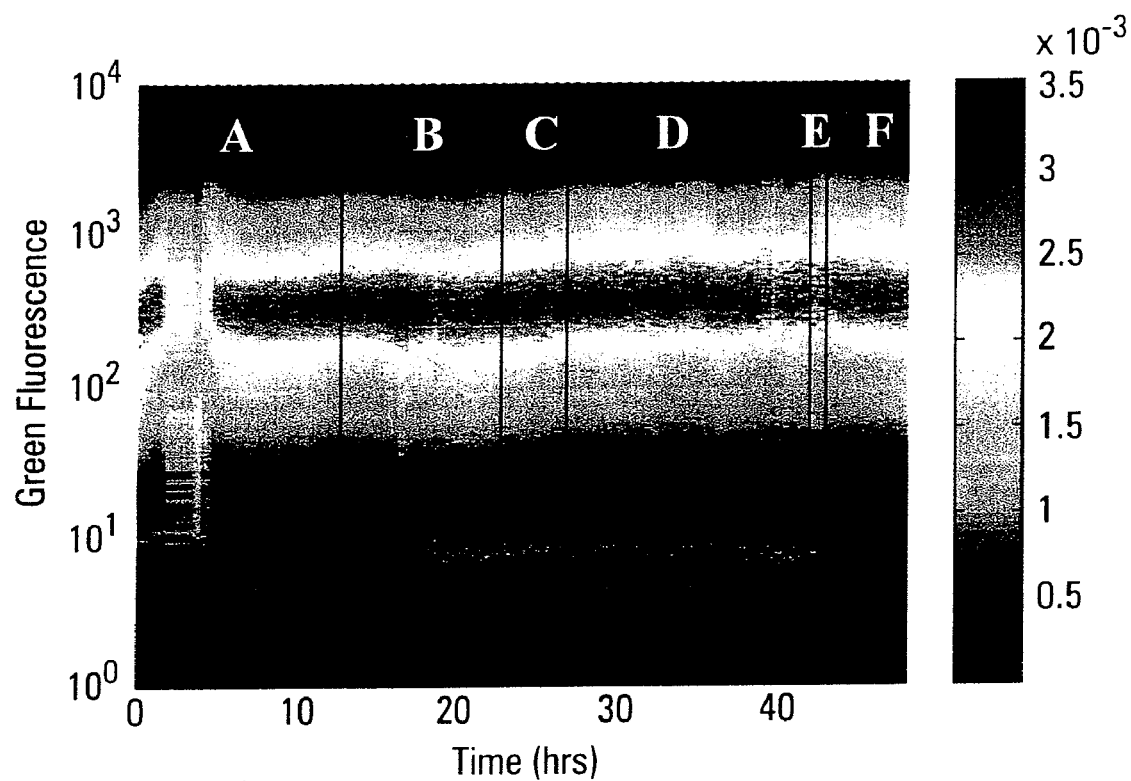
FIG. 12B is an example of a time profile for green fluorescent protein (GFP) of the yeast cells data of FIG. 11.

The cell counts, fluorescence, and light scattering measurements were monitored for the culture during all phases of growth. The average fluorescence and light scattering measurements and a comparison of the cell count data are shown in FIG. 11. A time profile of the FSC and green fluorescence are shown in FIG. 12A and FIG. 12B, respectively. During batch operation (indicated as A in FIG. 11), the cell count increases from $3 \times 10^5$ to about $1 \times 10^7$ cells/mL. During this time the size of the cells as indicated by FSC, increases and then quickly decreases as the cells begin to grow exponentially.

Once the chemostat began operation with a dilution rate of 0.22 $hr^{-1}$ and a glucose feed concentration of 6.6 g/L (indicated as region B in FIG. 11), the cell counts decreased to about $5 \times 10^6$ cells/mL. The distribution of the forward scatter remained fairly constant with much more large cells present than during exponential growth. The increase in large cells is probably because the growth rate is slower during growth in chemostat conditions than during batch growth. The value of the highest possible growth rate, $u_{max}$, decreases from 0.35 hr during batch growth to a value equal to the dilution rate, which is 0.22 $hr^{-1}$ in this case. The green fluorescence decreased slightly during this time possibly because the slower growth rate results in less selective pressure on the cells.

The dilution rate was then increased to 0.4 $hr^{-1}$ and the glucose concentration of the feed was decreased to 5.0 g/L (indicated as region C in FIG. 11). Because the dilution rate is higher than $u_{max}$, the reactor 104 is operating at washout conditions for this time. Therefore, one would expect a rapid decline in the cell count indicating that if the reactor was kept at these conditions for an extended time no cells would remain in the reactor 104. It was found that the cell number concentration decreased from $6 \times 10^6$ cells/mL to $2 \times 10^6$ cells/mL in just 3 hours.

Figure 13A:
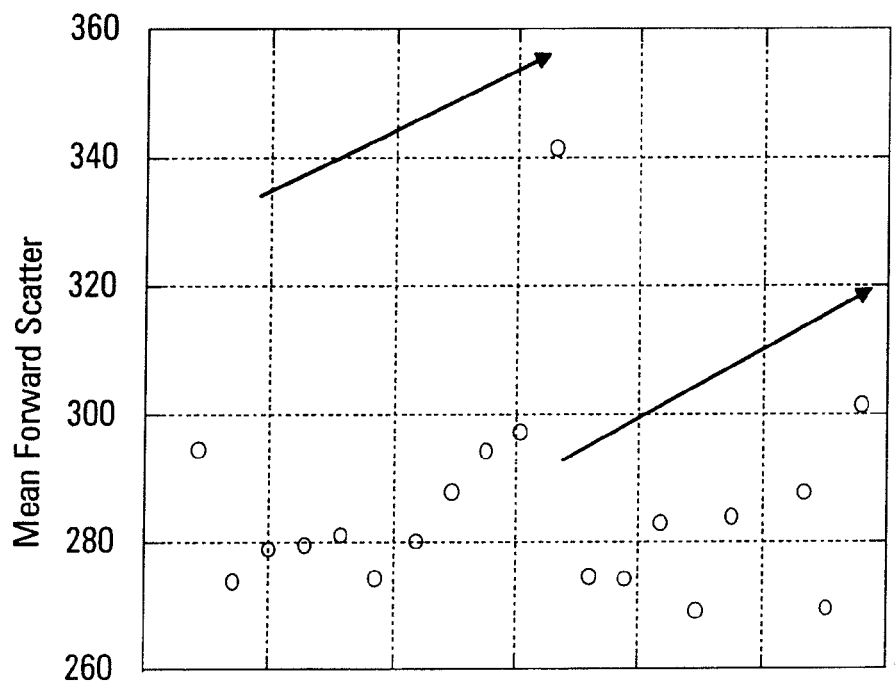
FIG. 13A is an example of a time profile (36 hours to 43 hours) for forward scatter (cell size) of the yeast cells data of FIG. 11.
Figure 13B:
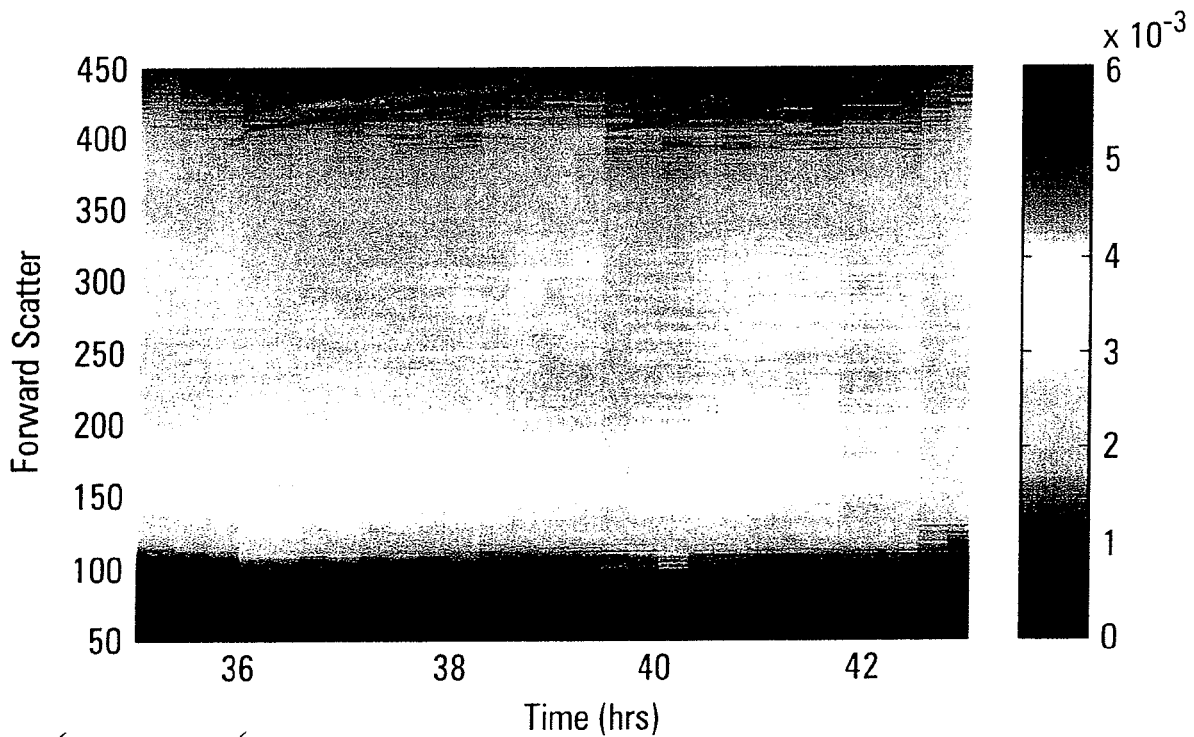
FIG. 13B is an example of a time profile (36 hours to 43 hours) for forward scatter (cell size) of the yeast cells data of FIG. 11.

The dilution rate was then lowered back to 0.22 $hr^{-1}$, which meant that the reactor 104 was not operating under wash out conditions anymore (indicated as region D in FIG. 11). As expected in this case the cell number concentration stabilized with the off-line counts just below $2 \times 10^6$ and the on-line counts around $9 \times 10^5$. Although the concentration of the on-line counts may have been slightly lower than recorded because the degassing unit 114 was emptying too quickly not allowing the injection of a complete sample. During this time the mean forward scatter measurements increased and decreased in an oscillatory fashion. These oscillations can be seen in FIGS. 13A and 13B, which is a magnified view of the average forward scatter versus time profile from this region. The arrows indicate increases of the forward scatter signal due to the formation of larger cells. It is thought that the sudden decreases may be due to the synchronization of the cells in the sample. The cells grow in a synchronized fashion producing a population of larger cells, then all these cells divide at the same time causing a decrease in the number of large cells present.

FIG. 14A through FIG. 14F illustrate the cytograms of the population as it moves through an oscillation. In FIG. 14A, the population of large cells is present. In FIG. 14B, the population of large cells is much smaller and the mean fluorescence of the sample is much less. In FIG. 14C and FIG. 14E, the cells continue to grow until a population of large cells is clearly present before cell division in FIG. 14F. Although the cell number concentration may be at a steady state, it would appear that the culture on an individual cell level may not be acting in a steady manner. Rather the distributions change dynamically as growth proceeds. Furthermore, after the dilution rate was decreased to 0.091 $hr^{-1}$ and the sugar concentration was lowered to 2.5 g/L (region F in FIG. 11) the size of the cells decreased again. This decrease was due to an increase in the amount of glucose available to the cells because of the decrease in the dilution rate.

It was found that the bioreactor system 100 can monitor the dynamics of cells in a chemostat. Furthermore, by monitoring the culture at the single-cell level it was found that even once the cell number density of the culture has approached steady state, the culture can still be behaving dynamically. By examining the forward scatter characteristics of the cells, it was found that the size distribution of the cells began oscillating. These oscillations appeared to be due to the cells growing in synchrony. This result would not have been discovered with traditional monitoring techniques that do not monitor the single-cell forward scatter characteristics of the culture.

Example 7

Bioreactor Enrichment with Yeast Clones Characterized by High PHB Expression Levels Using Direct PHB Staining The strain to be used is Saccharomyces cerevisiae D603 (REG1 mutant). In order to produce polyhydroxybutyrate (PHB) this strain needs to be transformed with two plasmids (p2DPT RK) and (p2DP-S(H)) by electroporation. Both plasmids contain the GAL1-10 bidirectional promoter, which regulates expression of the ketothiolase and reductase enzymes in plasmid p2DPT RK and the synthase enzyme in plasmid p2DP-S(H). The GAL promoter is induced by galactose, and therefore, the culture must be grown anaerobically in a selective medium composed of 1% glucose, 1% galactose and appropriate amounts of adenine as well as methionine and lysine amino acids. The culture pH is to be controlled at 4.5. After 24 hours of batch growth in a 500 mL bioreactor, the culture needs to be diluted using sterile media devoid of glucose and galactose to a concentration of $1 \times 10^4$ l/mL.

The following procedure needs to be repeated for 48-72 hours to enrich the bioreactor with mutant cells that have high PHB accumulation levels. First the post-bioreactor preparation chamber (postBPC) and the sample loop need to be washed thoroughly with citric-buffered saline (CBS) and bovine serum albumin (BSA) solutions. BSA is a high molecular weight protein, which is used to line the internal walls of the tubing to prevent cell adhesion and flow impediments. Then a sample from the bioreactor is to be degassed and passed to the postBPC. The lines before and after the postBPC need to be flushed of excess cells and this is achieved by washing the lines with CBS flowing through the filter of the postBPC. The cells are then treated with nile red to stain the PHB molecules. Nile red is to be fed to the postBPC for 1.5-2 minutes at a flow rate of 1 ml/minute. The cells are to be mixed with nile red for about 10 minutes to allow for the staining reaction to take place. The majority of the postBPC content is to be fed to the sample loop in 4-5 consecutive loading steps. After each loading step the contents of the sample loop are injected into the flow cytometer, analyzed and cells with the highest 5% level of fluorescence are sorted out and passed directly to the pre-bioreactor preparation chamber (preBPC). The sorted cells emerge diluted with sheath solution and are filtered in the preBPC. The sorted cells are then washed from the preBPC and recycled to the bioreactor using a stream of sterile media with reduced concentrations of glucose and galactose. Repeating this process for 48-72 hours would enrich the reactor with cells of desirable traits. The flow cytometer measurement of cell population fluorescence provides a direct measure of the enrichment of the bioreactor with desirable cells.

Example 8

Bioreactor Enrichment with Yeast Clones Characterized by High Copy Numbers of Plasmids Expressing an Integrated Protein Using GFP Expression as an Indirect Measure of the Protein Production The strain to be used is *Saccharomyces cerevisiae* D603 (REG1 mutant). In this example the yeast is to be transformed with a plasmid expressing an engineered protein of interest. The expression of the recombinant protein is regulated by the GAL1-10 promoter. On the other side of the promoter, a gene that encodes the green fluorescent protein GFP is regulated. This plasmid will be referred to as p2DP GP(H). GFP is a protein that can naturally fluoresce if excited with light of the appropriate wavelength, and therefore, it can be detected using a flow cytometer. Since the same promoter that regulates the recombinant protein regulates GFP expression, it is assumed that the GFP content of the cell is proportional to the protein content. This technique can be used to indirectly measure the PHB content of the cells by replacing plasmid p2DP ûS(H) in the previous example by plasmid p2DP GS(H). The GAL1-10 promoter in p2DP GS(H) regulates the expression of both the synthase enzyme and the GFP. Assuming that the synthase enzyme is the limiting factor in PHB production, the amount of PHB produced would depend on the expression of the synthase protein, which is proportional to the expression level of GFP. If synthase was not the limiting enzyme in the PHB production pathway, then other plasmids can be constructed where at one side of the promoter lies the GFP gene and on the other side lies a gene expressing the limiting enzyme (reductase or ketothiolase). While GFP provides only an indirect measure of the PHB content, it eliminates the need for PHB staining. This modification offers two important advantages: first it is a cheaper alternative since no nile red reagent is needed in this case, and second it reduces the pretreatment time significantly by removing the staining step.

The process is again very similar to the one described in the previous example and needs to be repeated for 36-48 hours before the cell population in the bioreactor is noticeably enriched with mutants offering high expression levels of the engineered protein. First, the postBPC and the sample loop are thoroughly washed with CBS and BSA. Then a sample of the bioreactor is degassed and passed to the postBPC. The lines before and after the postBPC are then washed of excess cells using CBS solution.

Afterwards, the contents of the postBPC are transferred to the sample loop. After loading the sample loop, the sample is injected into the flow cytometer analyzed and cells of interest are sorted out and passed to the preBPC. The preBPC is used to concentrate the cells and finally the cells are washed out from the preBPC and recycled back to the bioreactor using sterile medium with lowered substrate concentrations. Note that in this process the postBPC is used merely to adjust the concentration of the cells prior to loading them to the sample loop, therefore at sufficiently low bioreactor concentrations the postBPC unit can be bypassed. In this case the sample can be loaded directly from the degassing unit to the sample loop.

Example 9

Bioreactor Enrichment with Yeast Clones Hosting High Affinity Fluorescein-Binding Single-Chain Fv (scFv) Antibody Using Cell-Surface Display The yeast strain to be used in this example is again *Saccharomyces cerevisiae* D603. The yeast is to be transformed with a library of p2DP-Fv(H) plasmids. The plasmid expresses the fluorescein-binding single-chain antibody (scFv) under the strict regulation of the GAL1-10 promoter to avoid cell toxicity. The library of plasmids with mutations in the scFv fragment is achieved by error-prone polymerase chain reaction (PCR). The surface display of scFv using flow cytometry is possible using a fluorescently tagged antigen.

In this example, 500 mL batch culture of the transformed yeast is to be grown in a bioreactor aerobically for 24 hours at pH of 5.0. The growth media is composed 2% glucose, adenine, methionine, lysine and uracil with appropriate amounts of galactose to induce the production of scFv. At the end of the batch the culture is appropriately diluted to a concentration Of $1 \times 10^4$ l/mL using sterile medium devoid of substrates. The enrichment procedure is a repetitive procedure that needs to be performed for at least 48 hours. In this procedure the postBPC, the tubing and the sample loop are all washed thoroughly with CBS and BSA, the postBPC is filled up with a degassed sample of cells.

The lines before and after the postBPC are washed using CBS. Then a solution containing special fluorescent-tagged antigen is allowed to flow through the postBPC at a flow rate of 1 mL/min and for 1.5-2 minutes. The antigen solution is then allowed to come in contact with the cells in the microchamber for about 10-15 minutes. During this mixing period the antibodies on the surface of the yeast clones bind the fluorescent-tagged antigen with different affinities. Antibodies with high affinities bind more strongly to their target antigens and dissociate from the antigen only very slowly compared to lower affinity antibodies. A four fold difference in antibodies affinities due to the error-prone PCR has been reported in literature. The contents of the postBPC are then transferred to the sample loop. Once the sample loop is loaded, the sample is injected into the flow cytometer, analyzed and cells with high fluorescence, implying a high scFv affinity to the fluorescent-tagged antigen, are sorted and recycled back to the bioreactor. Prior to their recycling, the cells pass through the preBPC where they are concentrated. In order to remove the fluorescent antigen the cells are then treated with a saline solution at a pH that does not favor the scFv antibody-antigen binding. Finally preBPC contents are recycled to the bioreactor using a sterile medium with lowered concentrations of glucose and galactose.

The complete disclosures of all patents, patent applications including provisional patent applications, and publications, and electronically available material cited herein are incorporated by reference. The foregoing detailed description and examples have been provided for clarity of understanding only. No unnecessary limitations are to be understood there from. The invention is not limited to the exact details shown and described; many variations will be apparent to one skilled in the art and are intended to be included within the invention defined by the claims.

What is claimed is:

1. A method for accumulating cells of interest in a bioreactor, the method comprising:
   growing a heterogeneous population of cells in at least one bioreactor comprising a growth medium comprising a substrate, wherein the heterogeneous population comprises at least one cell of interest;
   removing a sample of cells from the bioreactor;
   measuring the cell density of the sample of cells; and
   adjustably providing fresh medium to the bioreactor to achieve a steady state cell density in the bioreactor that maintains a steady substrate concentration in the bioreactor, wherein achieving a steady state cell density in the bioreactor that maintains a steady substrate concentration in the bioreactor results in accumulation of cells of interest.

2. The method of claim 1 wherein measuring the cell density of the sample of cells comprises counting cells from a volume of the sample of cells.

3. The method of claim 2 wherein measuring the cell density of the sample of cells comprises counting cells in the sample of cells using a flow cytometer.

4. The method of claim 2 wherein measuring the cell density of the sample of cells comprises measuring the volume of the sample of cells.

5. The method of claim 2 wherein measuring the cell density of the sample of cells comprises counting cells in a predetermined volume of the sample of cells.

6. The method of claim 1 wherein the cell of interest possesses a growth rate that is greater than or equal to the growth rate of wild-type cells of the heterogeneous population grown in medium comprising the substrate.

7. A method for accumulating cells of interest in a bioreactor, the method comprising:
   growing a heterogeneous population of cells in at least one bioreactor comprising a growth medium comprising a feed substrate, wherein the heterogeneous population comprises at least one cell of interest;
   removing a sample of cells from the bioreactor;
   measuring the cell density of the sample of cells; and
   adjustably providing fresh medium comprising feed substrate to the bioreactor so that cell dilution resulting from providing fresh medium to the bioreactor maintains a concentration of substrate in the bioreactor that approximates the concentration of feed substrate in the fresh medium, wherein providing fresh medium comprising feed substrate to the bioreactor so that cell dilution resulting from providing fresh medium to the bioreactor maintains a concentration of substrate in the bioreactor that approximates the concentration of feed substrate in the fresh medium results in accumulating the cells of interest.

8. The method of claim 7 wherein measuring the cell density of the sample of cells comprises counting cells from a volume of the sample of cells.

9. The method of claim 8 wherein measuring the cell density of the sample of cells comprises counting cells in the sample of cells using a flow cytometer.

10. The method of claim 8 wherein measuring the cell density of the sample of cells comprises measuring the volume of the sample of cells.

11. The method of claim 8 wherein measuring the cell density of the sample of cells comprises counting cells in a predetermined volume of the sample of cells.

12. The method of claim 7 wherein the cell of interest possesses a growth rate that is greater than or equal to the growth rate of wild-type cells of the heterogeneous population grown in medium comprising the substrate.

* * * * *